(12) United States Patent
Teague et al.

(10) Patent No.: US 10,786,565 B2
(45) Date of Patent: Sep. 29, 2020

(54) POULTRY PROBIOTIC VACCINE COMPOSITIONS AND METHODS OF USE THEREOF

(71) Applicant: The Board of Trustees of the University of Arkansas, Little Rock, AR (US)

(72) Inventors: Kyle D. Teague, Little Rock, AR (US); Lisa Bielke, Little Rock, AR (US); Guillermo Tellez-Isaias, Fayetteville, AR (US); Billy Hargis, Fayetteville, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 0 days.

(21) Appl. No.: 16/311,065

(22) PCT Filed: Jul. 11, 2017

(86) PCT No.: PCT/US2017/041486
§ 371 (c)(1),
(2) Date: Dec. 18, 2018

(87) PCT Pub. No.: WO2018/013530
PCT Pub. Date: Jan. 18, 2018

(65) Prior Publication Data
US 2019/0343950 A1 Nov. 14, 2019

Related U.S. Application Data

(60) Provisional application No. 62/360,569, filed on Jul. 11, 2016.

(51) Int. Cl.
*A61K 35/747* (2015.01)
*C12N 7/00* (2006.01)
*A61K 39/255* (2006.01)

(52) U.S. Cl.
CPC .......... *A61K 39/255* (2013.01); *A61K 35/747* (2013.01)

(58) Field of Classification Search
None
See application file for complete search history.

(56) References Cited

U.S. PATENT DOCUMENTS

| | | | | |
|---|---|---|---|---|
| 2007/0178115 A1* | 8/2007 | Tang | ..................... | A61K 39/145 424/189.1 |
| 2007/0243212 A1 | 10/2007 | Doelling | | |
| 2009/0285920 A1* | 11/2009 | Lee | ........................ | A01N 63/02 424/754 |
| 2012/0034198 A1* | 2/2012 | Garner | ................. | A61K 35/741 424/93.44 |
| 2012/0156172 A1* | 6/2012 | Rho | ..................... | A61K 35/744 424/93.4 |

FOREIGN PATENT DOCUMENTS

| | | |
|---|---|---|
| EP | 1064947 A1 | 1/2001 |
| WO | 2015/197728 A1 | 12/2015 |

OTHER PUBLICATIONS

Alvarez-Olmos et al., Clinicial Infectious Diseases, vol. 32, pp. 1567-1576 (2001).
Anonymous, SAS/SHARE User's Guide—version 9.1 (2002).
Arshad et al., Medical Journal of Islamic Academy of Sciences, vol. 11, pp. 107-110 (1998).
Arvola et al., Pediatrics, vol. 104, No. 5, pp. 1-6 (1999).
Bacon et al., Poultry Science, vol. 79, pp. 1082-1093 (2000).
Baigent et al., Veterinary Immunology and Immunopathology, vol. 112, pp. 78-86 (2006).
Baskerville et al., Veterinary Record, vol. 130, pp. 395-398 (1992).
Bienenstock et al., Immunological Reviews, vol. 206, pp. 22-31 (2005).
Bienenstock, Environmental Health Perspectives, vol. 35, pp. 39-42 (1980).
Biloni et al., Poultry Science, vol. 92, pp. 2337-2346 (2013).
Borchers et al., Journal of Gastroenterology, vol. 44, pp. 26-46 (2009).
Calnek et al., Applied Microbiology, vol. 20, No. 5, pp. 723-726 (1970).
Calnek, Pathogenesis of Marek's Disease Virus Infection, pp. 25-55 (2001).
Cherian, World's Poultry Science Journal, vol. 67, No. 4, pp. 599-614 (2011).
Choct, British Poultry Science, vol. 50, pp. 9-15 (2009).
Churchill et al., Nature, vol. 215, pp. 528-530 (1967).
Dahiya et al., Animal Feed Science and Technology, vol. 129, pp. 60-88 (2006).
Dass et al., Neurogastroenterololgy and Motility, vol. 19, pp. 66-74 (2007).
De Geus, Journal of Immunology, vol. 188, pp. 41-144 (2012).
De Oliveira et al., Poultry Science, vol. 93, pp. 818-829 (2014).
Delgado et al., Poultry Science, vol. 93, No. 9, pp. 2363-2369 (2014).
Di Mauro et al., Italian Journal of Pediatrics, vol. 39, No. 15, pp. 1-7 (2013).
Dominguez-Bello et al., Microbes and Infection, vol. 10, pp. 1072-1076 (2008).
Drolet et al., Clinical Et Experimental Allergy, vol. 40, pp. 841-849 (2010).

(Continued)

*Primary Examiner* — Shanon A. Foley
(74) *Attorney, Agent, or Firm* — Kelly Reynolds

(57) ABSTRACT

Provided herein are compositions including a probiotic including at least one strain of live bacteria and a Marek's Disease vaccine. Compositions including a probiotic or a probiotic and a Marek's Disease vaccine may be administered to subjects, including poultry. The compositions may be administered in ovo to increase early lactic acid bacteria in the gastrointestinal tract of the subject, to decrease the gram negative bacteria in the gastrointestinal tract of the subject, to reduce the level of *Salmonella* in the gastrointestinal tract of the subject and to increase the body weight gain of the subject. Also provided are kits including a probiotic and a Marek's Disease vaccine.

16 Claims, 5 Drawing Sheets

(56) References Cited

OTHER PUBLICATIONS

Duerkop et al., Immunity, vol. 31, pp. 368-376 (2009).
Dunn et al., Avian Diseases, vol. 54, pp. 1038-1049 (2010).
Dunn et al., Avian Diseases, vol. 56, pp. 494-500 (2012).
Fagerland et al., American Journal of Anatomy, vol. 189, pp. 24-34 (1990).
Fagerland et al., Avian Disease, vol. 37, pp. 10-18 (1993).
Fallschissel et al., Ann. Occup. Hyg., vol. 53, No. 8, pp. 859-868 (2009).
Farnell et al., Poultry Science, vol. 85, pp. 1900-1906 (2006).
Galanis et al., Emerging Infectious Diseases, vol. 12, pp. 381-388 (2006).
Simeno, Vaccine, vol. 26S, pp. C31-C41 (2008).
Haghighi et al., Clinical and Vaccine Immunology, vol. 13, pp. 975-980 (2016).
Hahn-Didde et al., J. Appl. Poult. Res., vol. 25, No. 1, pp. 1-11 (2016).
Hashemzadeh et al., J. Agric. Sci. Tech., vol. 12, pp. 425-432 (2010).
Higgins et al., J. Appl. Poult. Res., vol. 14, pp. 345-348 (2005).
Higgins et al., Poultry Science, vol. 86, pp. 1662-1666 (2007).
Higgins et al., Avian Diseases, vol. 52, pp. 139-142 (2008).
Higgins et al., Poultry Science, vol. 89, pp. 243-247 (2010).
Howarth et al., Nutrients, vol. 5, pp. 58-81 (2013).
Isolauri et al., Gut, vol. 50, Suppl. III, pp. iii54-iii59 (2002).
Kallapura et al., Avian Pathology, vol. 43, pp. 305-309 (2014).
Kallapura et al., Journal of Microbiology Research and Reviews, vol. 2, No. 1, pp. 6-11 (2014).
Kallapura et al., Veterinary Medicine: Research and Reports, vol. 5, pp. 59-73 (2014).
Kiser, Journal of Animal Science, vol. 42, pp. 1058-1072 (1976).
Leach et al., FEMS Microbiology Letters, vol. 171, pp. 203-207 (1999).
Lyte, BioEssays, vol. 33, pp. 574-581 (2011).
Martin et al., Beneficial Microbes, vol. 1, No. 4, pp. 367-382 (2010).
McFall-Ngai, Nature, vol. 445, p. 153 (2007).
Menconi et al., Poultry Science, vol. 90, No. 3, pp. 561-565 (2011).
Menconi et al., International Journal of Poultry Science, vol. 12, No. 2, pp. 72-75 (2013).
Metchnikoff, Journal of Abnormal Psychology, pp. 301-302 (1908).
Molinaro et al., Gastroenterol. Clin. N. Am., vol. 41, pp. 843-854 (2012).
Moran, PNAS, vol. 104, Suppl. 1, pp. 8627-8633 (2007).
Nair, Veterinary Journal, vol. 170, pp. 175-183 (2005).
Neish, Gastroenterology, vol. 136, pp. 65-80 (2009).
NRC, Nutrient Requirements of Poultry, 9th revised Edition, pp. 19-39 (1994).
NRC, Nutrient Requirements of Poultry, 9th Revised Edition, pp. 19-45 (1994).
O'Hara et al., EMBO Reports, vol. 7, pp. 688-693 (2006).
Parker, Journal of Nutrition, vol. 120, No. 6, pp. 639-648 (1990).
Parvizi et al., Animal Health Research Reviews, vol. 11, No. 2, pp. 123-134 (2010).
Qiu et al., J. Anim. Sci., vol. 90, pp. 2639-2651 (2012).
Saif, Diseases of Poultry, 11th Edition, chapter 15, pp. 405-564 (1970).
Sakamoto et al., Journal of Surgical Research, vol. 94, pp. 99-106 (2000).
Salminen et al., Journal of Pediatrics, vol. 149, pp. S115-S120 (2006).
Segawa et al., PLOS ONE, vol. 6, No. 8, article e23278 (2011).
Sekirov et al., Physiol. Rev., vol. 90, pp. 859-904 (2010).
Siegmann et al., Avian Pathology, vol. 9, pp. 21-32 (1980).
Silva et al., Avian Diseases, vol. 54, No. 2, pp. 862-869 (2010).
Smialek et al., Polish Journal of Veterinary Sciences, vol. 14, No. 2, pp. 291-297 (2011).
Tao et al., Am. J. Physiol. Cell Physiol., vol. 290, pp. C1018-C1030 (2006).
Teague et al., "Effect of a Lactic Acid Bacteria-Based Probiotic in ovo on Hatchability and Recovery of Bacteria in Broiler Chicks", p. 1 (2015).
Teillant et al., Choices, vol. 30, pp. 1-11 (2015).
Tellez et al., Food Research International, vol. 45, pp. 628-633 (2012).
Tellez, Frontiers in Veterinary Science, vol. 1, article 3, pp. 1-6 (2014).
Tlaskalova-Hogenova et al., Cellular and Molecular Immunology, vol. 8, pp. 110-120 (2011).
Torres-Rodriguez et al., J. Appl. Poult. Res., vol. 16, pp. 635-641 (2007).
Vanderpool et al., Inflamm. Bowel Dis., vol. 14, pp. 1585-1596 (2008).
Vicente et al., J. Appl. Poult. Res., vol. 16, pp. 361-364 (2007).
Vicente et al., Avian Diseases, vol. 52, No. 1, pp. 143-146 (2008).
Walter et al., PNAS, vol. 108, Suppl. 1 pp. 4645-4652 (2011).
Wathes et al., Veterinary Record, vol. 123, pp. 590-594 (1988).
White et al., Rev. Sc. Tech. Off. Int. Epiz., vol. 16, No. 2, pp. 525-541 (1997).
Witter et al., Avian Diseases, vol. 24, pp. 210-232 (1980).
Wolfenden et al., International Journal Poultry Science, vol. 6, pp. 493-496 (2007).
Yitbarek et al., Poultry Science, vol. 92, pp. 2299-2310 (2013).
You et al., Frontiers in Microbiology, vol. 5, p. 284 (2014).
Yu et al., Journal of Microbiology, vol. 50, No. 4, pp. 613-617 (2012).
Zar, Biostatistical Analysis, 2nd edition, Chapter 5, pp. 40-60 (1984).
Zareie et al., Gut, vol. 55, pp. 1553-1560 (2006).
Caly et al, 2015, Frontiers in Mivrobiology, vol. 6, pp. 1-12.
Reddy et al, 1996, Vaccine, vol. 14, No. 6, pp. 469-477.
Teague et al, 2017, Poultry science, vol. 96, No. 7, pp. 2074-2082.

\* cited by examiner ately inject twice at the time of egg transfer from incubators to hatching cabinets (~d18E) due to markedly increased highly technical injection equipment, doubling the risk of physical damage to the embryo by double injection, and at least doubling the chances of unintended contamination with opportunistic bacterial pathogens which are prevalent in hatchery environments.

POULTRY PROBIOTIC VACCINE COMPOSITIONS AND METHODS OF USE THEREOF

CROSS-REFERENCE TO RELATED APPLICATIONS

This application is a 35 U.S.C. 371 national application of international application no. PCT/US2017/041486 filed Jul. 11, 2017, which claims priority or the benefit under 35 U.S.C. of U.S. provisional application No. 62/360,569 filed Jul. 11, 2016, the contents of which are fully incorporated herein by reference.

REFERENCE TO A DEPOSIT OF BIOLOGICAL MATERIAL

This application contains a reference to a deposit of biological material, which deposit is incorporated herein by reference.

INTRODUCTION

Under commercial conditions, millions of poultry including chickens and turkeys hatch in a hostile environment, and are exposed for several hours to heat stress and potential pathogenic bacteria in the hatcheries. Increased stress along with the potential abundance of pathogens in the hatching cabinet leads to ideal conditions for pathogen colonization. It is generally accepted that the natural route of transmission of zoonotic pathogens such as *Salmonella*, is fecal-oral (White et al., 1997; Galanis et al., 2006). However, published studies have also suggested that airborne transmission of *Salmonella* in poultry is possible (Wathes et al., 1988; Baskerville et al., 1992; Leach et al., 1999; Fallschissel et al., 2009).

The architecture of the avian respiratory tract is an important component explaining the susceptibility and resistance to infectious agents. In day old avian livestock, no or very few infiltrating lymphocytes are seen in the primary bronchi region (Fagerland and Arp, 1990; Smialek et al., 2011) and it is not until 3-4 weeks of age the lymphoid nodules are developed at these locations (Fagerland and Arp, 1993; Drolet et al., 2010). During the following week, the number of IgG, IgA or IgM-producing cells continues to increase, however, the bronchial-associated lymphoid tissue (BALT) is not mature until chickens are 6-8 weeks old (Bienenstock, 1980; Bienenstock and McDermott, 2005; De Geus, 2012). Hence, commercial neonate poultry are extremely susceptible to airborne pathogens, regardless of whether or not they are respiratory or enteric bacteria (Arshad et al., 1998).

To help prevent disease and pathogenic infection in poultry, use of probiotics has emerged as a useful strategy. Over a century ago, Eli Metchnikoff proposed the groundbreaking idea to ingest viable bacteria to improve health (Metchnikoff, 1908). This concept is more appealing today, since antimicrobial resistant bacteria have become a problem in many countries (Kiser, 1976; Dahiya et al., 2006; Teillant and Laxminarayan, 2015). The imminent ban of antibiotics in animal feed creates a challenging scenario for expansion of alternative prophylactics (Parker, 1990; Dahiya et al., 2006; You and Silbergeld, 2014). Probiotics and direct-fed microbials are becoming accepted as one of the best tools for maintaining gastrointestinal health and promoting performance in poultry raised without antibiotics (Dominguez-Bello and Blaser, 2008). In addition to improving intestinal microbial balance, metabolism, and gut integrity (Isolauri et al., 2002; Salminen and Isolauri, 2006), studies have also shown that some probiotics have anti-inflammatory (Borchers et al., 2009; Lyte, 2011), anti-oxidant (Farnell et al., 2006; Tao et al., 2006; Zareie et al., 2006; Segawa et al., 2011; Howarth and Wang, 2013), and enhanced barrier integrity properties (Yu et al., 2012). Furthermore, several researchers have confirmed benefits of probiotics on innate immunity (Alvarez-Olmos and Oberhelman, 2001; Vanderpool et al., 2008; Molinaro et al., 2012) as well as humoral immunity (Arvola et al., 1999; Haghighi et al., 2006; Howarth and Wang, 2013).

Although probiotics have shown promise in promoting healthy microflora development and prevention of disease in poultry when directly fed to the animals, such administration may often be too late to optimally protect animals from the hostile conditions immediately following hatching. In ovo administration of probiotics presents one possible means of ensuring that probiotics may exert their beneficial effects prior to or during hatching.

However, the only practical and reliable way to administer a probiotic in ovo would be mixing it with the diluent of the Marek's disease (MD) vaccine given the unacceptably high risks of infection and damage to the egg if more than one in ovo injection per egg was performed. The preferred site of delivery for the probiotic is the avian amnion, which is also the site of delivery of the Marek's disease vaccine. Just prior to pipping (breaking through the egg shell just before hatch), the avian embryo swallows residual amnionic fluid, providing the very first opportunity to inoculate the gastrointestinal tract with beneficial microflora. While single injections into the avian amnion with conventional in ovo vaccination causes only small losses in terms of hatchability, it would be a significant obstacle to inject twice at the time of egg transfer from incubators to hatching cabinets (~d18E) due to markedly increased highly technical injection equipment, doubling the risk of physical damage to the embryo by double injection, and at least doubling the chances of unintended contamination with opportunistic bacterial pathogens which are prevalent in hatchery environments.

MD is a lymphoproliferative disease of domestic chickens caused by an oncogenic α-herpesvirus (Churchill and Biggs, 1967; Calnek, 2001). The disease is associated with lymphomas, neurologic manifestations, and immune suppression (Calnek, 2001). Without a question, MD has been a major concern to the poultry industry for over half a century (Nair, 2005), and the modern poultry industry as we know it today, would not exist without the development of MD vaccines (Baigent et al., 2006; Gimeno, 2008; Parvizi et al., 2010; Silva et al., 2010; Dunn and Silva, 2012). The virus is so abundant and stable in the environment, that vaccination at the hatchery is the only effective method to control MD in commercial flocks (Witter et al., 1980, 2005; Baigent et al., 2006; Dunn et al., 2010). Due to the significant economic and immunosuppression impact, modern commercial chickens are vaccinated before they leave the hatchery.

Although combining a probiotic with the MD vaccine would seem to be a straightforward way of delivering both in ovo, it is known in the art that the diluent of the MD vaccine is sensitive to the addition of additional agents. For example, it is known that lyophilization and stability are difficult issues with MD vaccines and that proper care and handling of MD vaccines are critical for viability and efficacy. See, e.g., Calnek et al., *Applied Microbiology* 20:5 723-726 (1970); 11th edition of Diseases of Poultry, Editor: Y. M. Saif, Chapter 15 by Aly M. Fadly. There, thus, is a need in the art for compositions and methods that can deliver probiotics in ovo without adversely affecting the efficacy of the Marek's disease (MD) vaccine.

SUMMARY

Compositions are provided and may include a probiotic, a Marek's Disease vaccine, and, optionally, a diluent.

In another aspect, methods of treating a subject with the compositions described herein are provided. The methods may include administering to the subject any one of the compositions described herein comprising a probiotic and a Marek's Disease vaccine. The methods may also include treating a subject by administering a probiotic bacterium to a poultry subject in ovo.

In a further aspect, kits are provided. The kits may include a probiotic, a Marek's Disease vaccine, and, optionally, a diluent.

DETAILED DESCRIPTION

Figure 1:
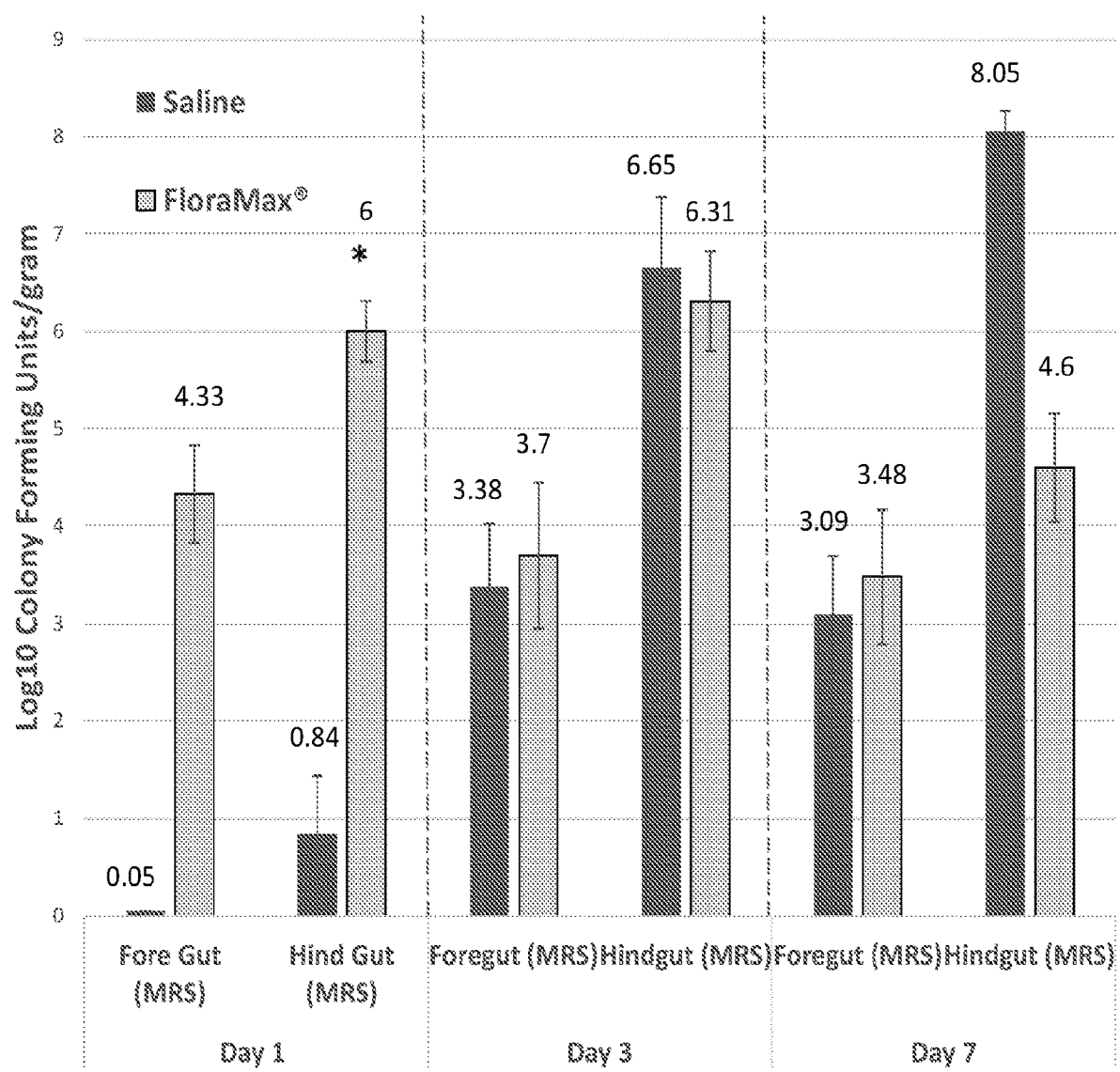
FIG. 1 is a graph showing the lactic acid bacterial recovery from the foregut and the hindgut of the gastrointestinal tract on days 1, 3, and 7 after hatch after in ovo inoculation with saline or the FloraMax probiotic. * indicates significantly different means (p<0.05).

The present inventors have surprisingly discovered that enteric-adapted lactic acid bacteria such as those found in FloraMax®-B11 do not interfere with commercial Marek's disease (MD) vaccine protective efficacy in chickens when applied in combination by in ovo injection. Moreover, such bacterial isolates do not affect hatchability, markedly reduce Gram negative bacterial populations at placement, increase resistance to *Salmonella enteritidis*, and increase 7 day body weights of broiler chicks.

One of the two major concerns the inventors addressed was whether in ovo administration of enteric-adapted lactic acid bacteria, such as those found in FloraMax®-B11, would negatively affect MD vaccine protective efficacy. As shown in the Examples, the inventors demonstrated that there was no negative impact and even possibly a small improvement in MD vaccine protective efficacy when the probiotic was combined with the MD vaccine. As far as the inventors are aware, this is the first report showing the possibility of combining a probiotic with an in ovo MD vaccine showing no negative effect. The other major concern with in ovo application of a probiotic was on broiler hatchability, but in every trial conducted the probiotic also showed no negative effects on hatchability.

In the present application, the inventors also observed that embryos, which received the probiotic before hatch, had a significant reduction in lactose positive Gram negative bacteria when compared with saline treated chickens (See, e.g., Table 3). Although there is extensive evidence demonstrating that probiotics such as FloraMax®-B11 are able to control Salmonellae infections in poultry in both laboratory and commercial conditions (Farnell et al., 2006; Higgins et al., 2007, 2008, 2010; Vicente et al., 2007; Menconi et al., 2011, 2013; Tellez et al., 2012; Biloni et al., 2013; Delgado et al., 2014), the present application further demonstrates that probiotics such as FloraMax®-B11 are efficacious when administered in ovo. The results disclosed in the present application suggest that in ovo administration of probiotics FloraMax®-B11 does not negatively affect turkey herpesvirus (HVT) vaccine efficacy or hatchability of the chickens, and improves body weight (BW) and intestinal integrity during the first 7 days of life while decreasing *Salmonella enteritidis* (SE) intestinal load in broiler chickens.

Probiotic vaccine compositions are provided. The compositions may include a probiotic and a Marek's Disease vaccine. Optionally, the compositions may further include a diluent.

The probiotic may include a lactic acid bacteria or any combination of two or more lactic acid bacterial species. The lactic acid bacteria may have been selected for gut adaptation in poultry. Several approaches for selection of gut adapted poultry Lactic Acid Bacteria have been successfully demonstrated. Bielke and co-workers demonstrated an in vitro competition assay that was successful for rapid screening of millions of candidates to fewer isolates for in vivo testing (Bielke et al., *Poult. Sci.* 82:9 1378-82 (2003)). Further in vivo evaluation has been demonstrated in a number of publications including Torres-Rodriguez et al. *Poult. Sci.* 85:100-100 (2005) Higgins et al., *Poult. Sci.* 85:38-39 (2006); and Higgins et al., *Poult. Sci.* 86:2315-2321 (2006). The primary indicator for success in these studies was based on competitive exclusion of a common Gram negative *Salmonella* pathogen. Further evaluations have included effects of selected LAB on performance, bone quality and enteric morphometric analysis (Gutierrez-Ruentes et al., *International Journal of Poultry Science* 12:322-327 (2013); Biloni et al., Poult. Sci. 92:2337-2346 (2013).

The probiotic may include lactic acid bacterial species selected from the genera *Lactobacillus, Lueconostoc, Weissella, Pediococcus, Enterococcus, Staphylococcus* or combinations thereof. In some embodiments, the probiotic may include lactic acid bacteria from the genus *Weissella* and lactic acid bacteria from the genus *Pediococcus*. Optionally, the probiotic may include the lactic acid bacteria species *Weissella cibaria*, the lactic acid bacteria species *Pediococcus acidilactici*, or both species. Other lactic acid bacterial species may also be used in accordance with the present invention including, without limitation, *Lueconostoc mesenteroides* and *Lactobacillus plantarum* 1, *Enterococcus faecium* and *Staphylococcus epidermis*. Where more than one species of bacteria is used as the probiotic, different ratios of the bacterial species may be combined. For example, when considering probiotics with two bacterial species, the ratio of strains may be approximately 1:1; 1:2; 1:3; 1:4; 1:5; 1:6; 1:7; 1:8; 1:9; 1:10 (first bacterial species to second bacterial species) or approximately 1:1; 1:2; 1:3; 1:4; 1:5; 1:6; 1:7; 1:8; 1:9; 1:10 (second bacterial species to first bacterial species). In FloraMax®-B11, the ratio of

*Weissella cibaria* to *Pediococcus acidilactici* used is about 1:4, although other ratios (i.e., 1:1; 1:2; 1:3; 1:4; 1:5; 1:6; 1:7; 1:8; 1:9; 1:10) are also expected to be effective in accordance with the present invention.

The probiotic may include the bacterial species present in the commercial product FloraMax®-B11 (NRRL-FM46 B-50961 and NRRL-FM18 B50964), either individually or in combination. FloraMax®-B11 is a defined lactic acid bacteria probiotic culture that has demonstrated an accelerated development of normal microflora in chickens and turkeys. It provides increased resistance to *Salmonella* spp. infections (Farnell et al., 2006; Higgins et al., 2007, 2008, 2010; Vicente et al., 2007; Menconi et al., 2011, 2013; Tellez et al., 2012; Biloni et al., 2013; Delgado et al., 2014), reduces idiopathic diarrhea in commercial turkey brooding houses (Higgins et al., 2005), as well as facilitates increased performance and reduced costs in poultry (Torres-Rodriguez et al., 2007; Vicente et al., 2008).

Figure 5:
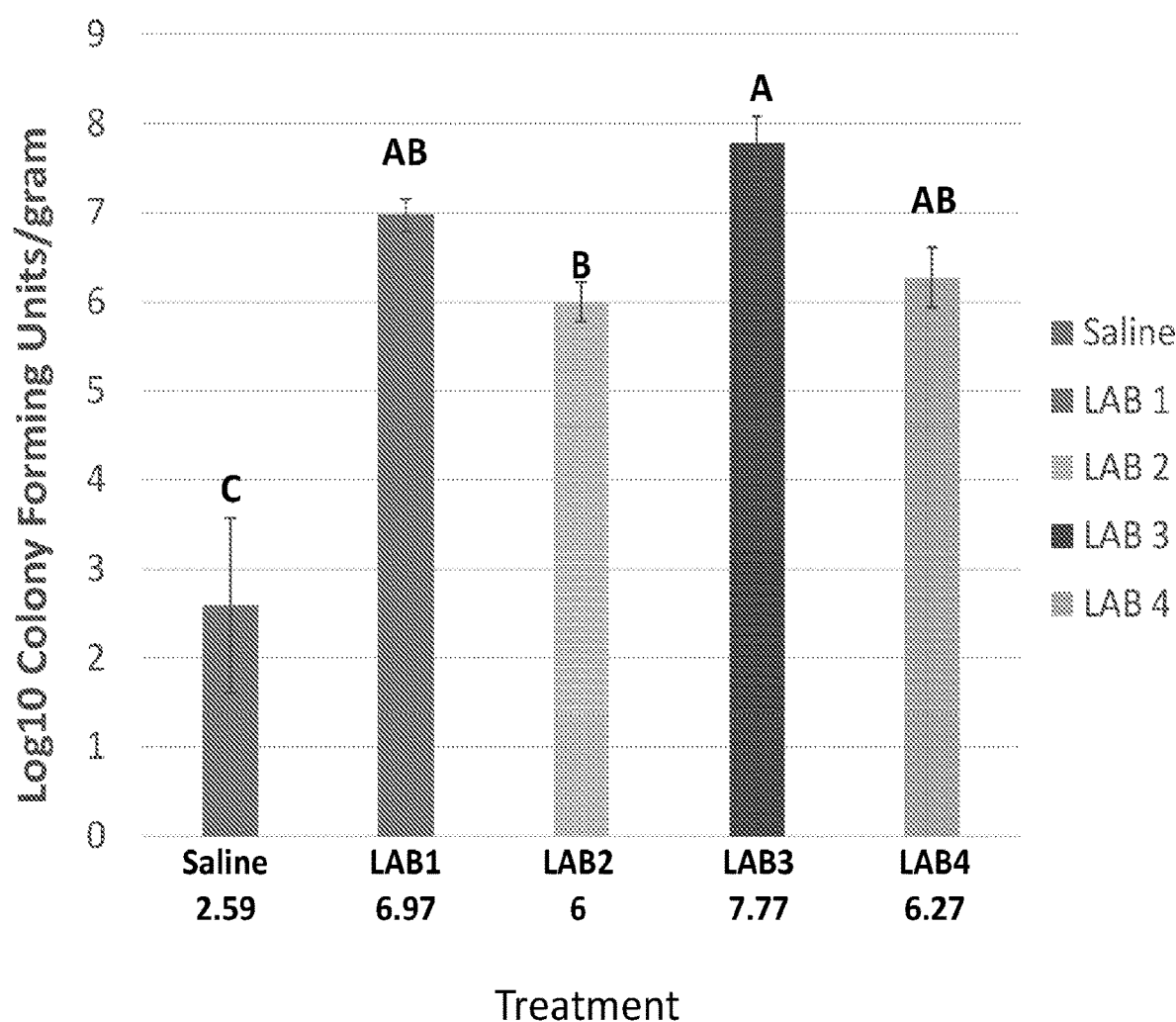
FIG. 5 is a graph showing the lactic acid bacterial recovery from the gastrointestinal tract on day 1 after hatch after in ovo inoculation with saline or the indicated probiotic bacteria. A, B, C above the bar indicates significantly different means for different letters (p<0.05).

The inventors also disclose four additional strains of lactic acid bacterial species (LAB 1-4). As shown in FIG. 5, the inventors provide evidence that LAB strains 1-4 are effective for prenatal gut colonization. LAB strains 1-4 are cocci species and thus the probiotic may also include one or more cocci species. The inventors expect a variety of lactic acid bacterial species and strains can be selected for use in the compositions and methods provided herein.

The Marek's Disease vaccine may include any vaccine that provides protection against Marek's Disease in poultry. The Marek's Disease vaccine may be cell-free, cell-associated, or combinations including both cell-free and cell-associated versions of the vaccine. Several different types of Marek's Disease vaccines are well known in the art, both individually and in various combinations, and may be used in accordance with the present invention. The most common Marek's Disease vaccines are attenuated serotype 1 MDV, naturally avirulent HVT, serotype 2 MDV viruses, and combinations thereof. The serotype 2 viruses are commonly combined with HVT strains to take advantage of synergistic activity that has been well-documented in the art.

The Marek's Disease vaccine may include an HVT vaccine. The HVT vaccine may include any HVT strain including, without limitation, the FC-126 strain of turkey herpesvirus. Optionally, the FC-126 strain of turkey herpesvirus may be present in a commercially-available vaccine such as, without limitation, Merials's Marek's Disease Vaccine Select, Serotype 3, Live Virus, HVT. The Marek's Disease vaccine may include an attenuated MDV strain. The attenuated MDV strain may include SB-1, 301B/1, R2/23, CVI988 or combinations thereof. The Marek's Disease vaccine may include a bivalent vaccine including a combination of HVT and attenuated MDV strains or combinations including serotype 1 and serotype 2 MDV strains.

The diluent may include any solution used to deliver a Marek's Disease vaccine. The diluent may include a carbohydrate, phosphate buffer, NZ amine, NZ Amine AS, or any combination thereof. The carbohydrate may be sucrose. Optionally, the diluent may include dimethyl sulfoxide. Preferably, the diluent is isotonic. The diluent may include any diluent included with a commercially-available Marek's Disease vaccine. In some embodiments, the diluent may include the diluent included with Merials's Marek's Disease Vaccine Select, Serotype 3, Live Virus, HVT.

Methods of treating a subject are also provided. The methods may include administering to a subject any one of the compositions described herein including a probiotic and a Marek's Disease vaccine. The subjects may be any species that may contract Marek's Disease or any species where administration of a Marek's Disease vaccine may be beneficial. Suitable subjects include, without limitation, poultry such as chickens and turkeys. Additional methods include administering a probiotic to a subject in ovo. Suitably the probiotic contains bacterial strains NRRL-FM46 B-50961 and/or NRRL-FM18 B50964. Such administration does not affect hatchability, but does result in increased body weight by 3 to 7 days after hatch. In ovo administration of probiotics also increases the number of lactic acid bacteria, decreases the number of gram negative bacteria and decreases the number of *Salmonella* in the gastrointestinal tract after hatch. The increase in body weight may be at least 3, 4, 5, 6, 7, 8, 9, 10, or even more than 10% as compared to a control subject not administered a probiotic in ovo by days 3, 5, or 7 after hatch.

The compositions may be administered in ovo to 15, 16, 17, 18, 19, 20, 21 or 22 day old embryos. Alternatively or in combination, the compositions may be administered at or after hatching. Useful dosages of the Marek's Disease vaccine in accordance with the present invention will vary depending on the age, weight and species of the subject, and the mode and route of administration. For commercially-available Marek's Disease vaccines, dosages will correspond to what is instructed on the label or other instructions. Generally, doses in excess of 500, 1000, 1500, 2000, 2500, 3000, 3500, 4000, or 5000 plaque-forming units/animal are suitable. The composition may be administered in any dose sufficient to evoke an immune response.

Useful dosages of the probiotic in accordance with the present invention will vary depending on the age, weight and species of the subject, and the mode and route of administration. Doses in excess of $10^2$, $10^3$, $10^4$, $10^5$, $10^6$, $10^7$, or $10^8$ colony-forming units (CFUs) may be used. Suitably $10^3$-$10^5$ colony-forming units are administered to each egg. When the probiotic is administered without the Marek's Disease vaccine, higher amounts of the probiotic may be used, such as $10^3/10^8$ cfu/egg.

Kits are provided. The kits may include any of the compositions described herein. The kits may include a probiotic and a Marek's Disease vaccine. Optionally, the kits may further include a diluent. Within the kit, the probiotic and Marek's Disease vaccine may be in the same compartment (such as an ampule) or may be in separate compartments. The diluent within the kit may be in a separate compartment from the probiotic and Marek's Disease vaccine or it may be within the same compartment as the probiotic and/or Marek's Disease vaccine. The probiotic and Marek's Disease vaccine may further exist as a solution or a solid such as a lyophilized powder.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

As used herein, "about," "approximately," "substantially," and "significantly" will be understood by persons of ordinary skill in the art and will vary to some extent on the context in which they are used. If there are uses of these terms which are not clear to persons of ordinary plus or minus ≤10% of the particular term and "substantially" and "significantly" will mean plus or minus >10% of the particular term.

The following examples are meant only to be illustrative and are not meant as limitations on the scope of the invention or of the appended claims.

EXAMPLES

Example 1—Effects of In Ovo Administration of Lactic Acid Bacteria

This Example describes in ovo administration of lactic acid bacteria, and in particular gut adapted lactic acid bacteria, on early hatchling performance and ability to resist colonization with pathogenic bacteria or bacteria that will not be beneficial to the feed efficiency of the young chick. We found that in ovo administration of probiotic lactic acid bacteria did not negatively impact hatchability, increased the colonization of the gastrointestinal tract with lactic acid bacteria, decreased the recovery of gram negative bacteria from the gastrointestinal tract, decrease the recovery of *Salmonella* from the gastrointestinal tract and resulted in significantly increased body weights by 3 to 7 days after hatch. These results demonstrate the benefits of in ovo probiotic administration to early chick gastrointestinal health.

Figure 2:
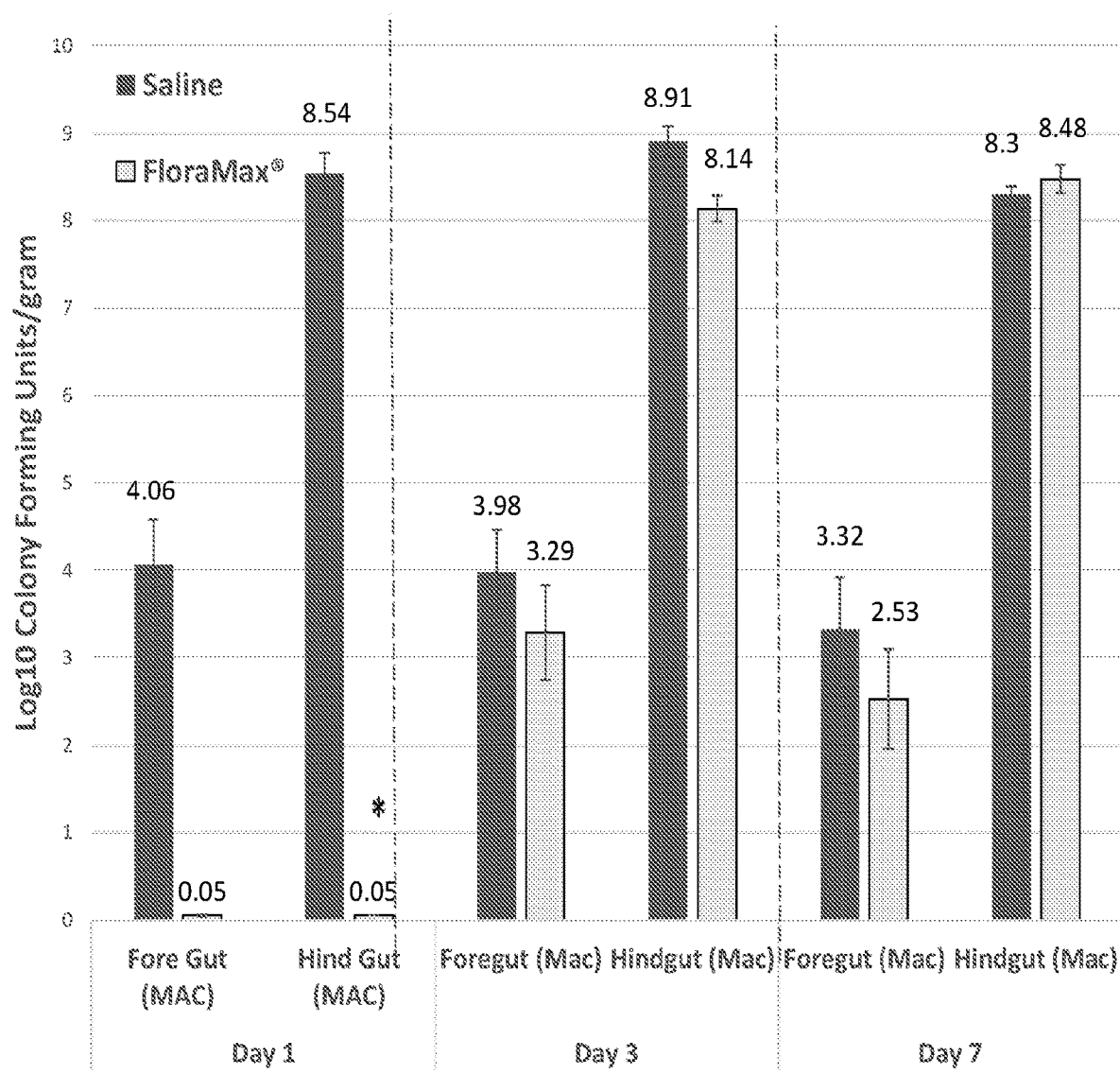
FIG. 2 is a graph showing the gram negative bacterial recovery from the fore gut and hind gut of the gastrointestinal tract on days 1, 3, and 7 after hatch after in ovo inoculation with saline or the FloraMax probiotic. * indicates significantly different means (p<0.05).

In Experiment 1, 150 eggs were injected with 200 µL/egg sterile saline and 150 eggs were injected with 200 µL/egg of FloraMax® into the amnion at 19 days of embryogenesis. The probiotic contained $2 \times 10^4$ CFU/200 µL consisting of a mixture of two gastrointestinal tract adapted bacteria. At hatch the chicks were randomly allocated to individual floor pens with 15 birds/pen and provided with food and water ad libitum. On days 1, 3 and 7 after hatch the effects on gastrointestinal tract recovery of selected bacterial groups was evaluated by selecting 12 chicks from each treatment group and foregut and hindgut samples were obtained and used to evaluate the bacterial recovery. FIG. 1 shows the lactic acid bacterial recovery from the foregut and hindgut at days 1, 3 and 7 after hatch. The chicks receiving probiotics in ovo had significantly increased lactic acid bacteria in both foregut and hindgut at day 1, but these differences were not seen at later times post-hatch. As shown in FIG. 2, the chicks receiving probiotics in ovo also had significantly lower levels of gram negative bacteria in both the foregut and hindgut at day 1 after hatch and in the hindgut at day 3 after hatch, but these differences were lost by day 7 after hatch.

Figure 3:
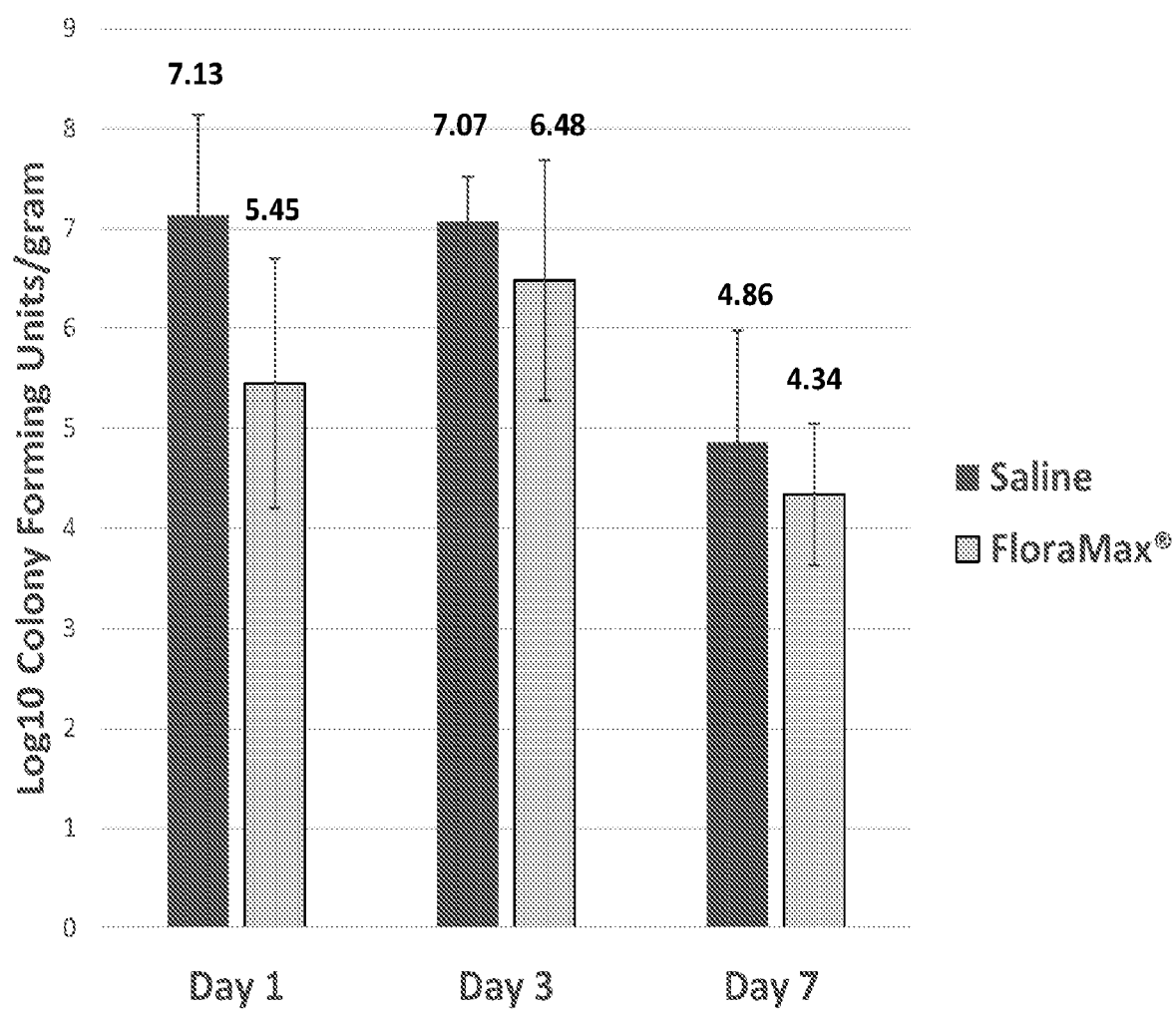
FIG. 3 is a graph showing the amount of *Salmonella* recovery from cecal samples on days 1, 3, and 7 after hatch after in ovo inoculation with saline or the FloraMax probiotic. * indicates significantly different means (p<0.05).
Figure 4:
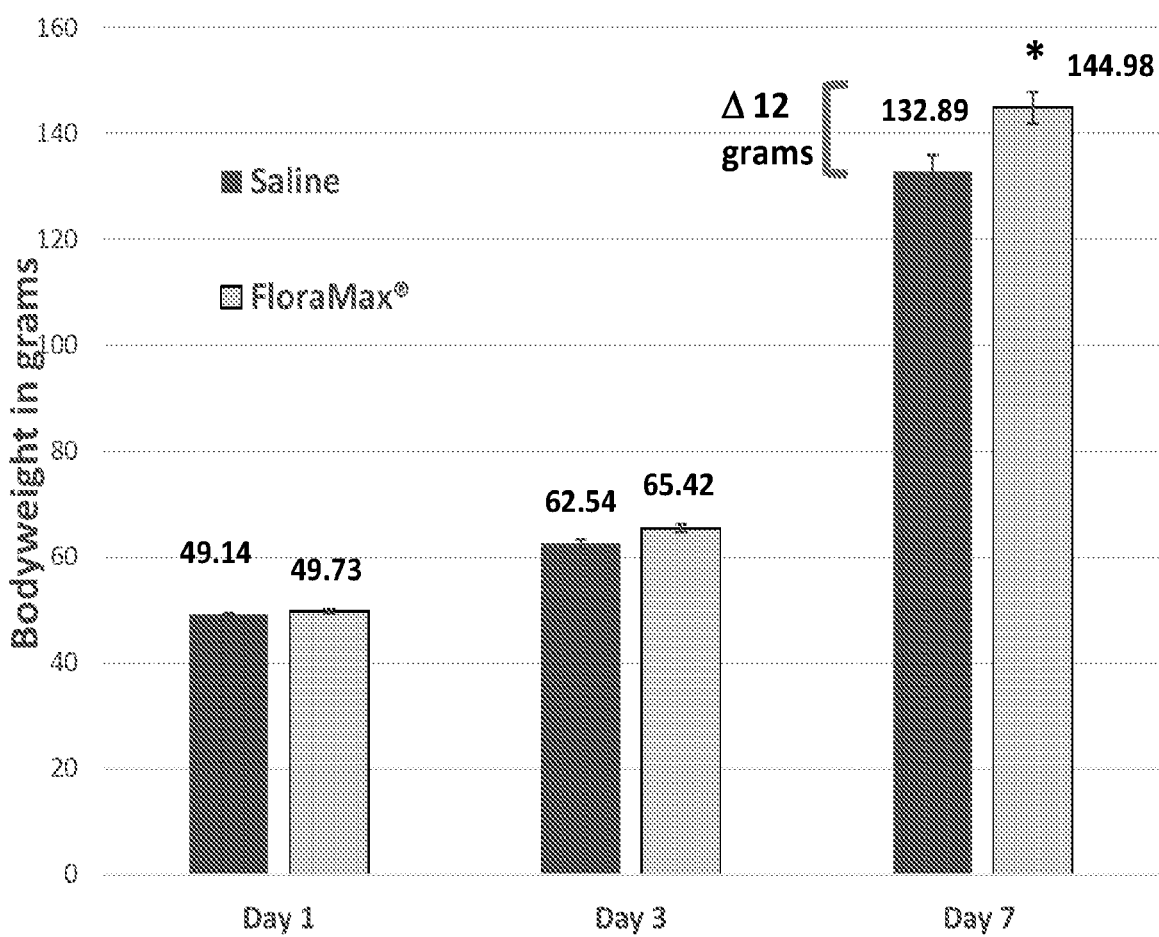
FIG. 4 is a graph showing the average body weight of all birds per treatment group at days 1, 3, and 7 after hatch after in ovo inoculation with saline or the FloraMax probiotic. * indicates significantly different means (p<0.05).

Experiment 2 was performed to evaluate whether administration of the probiotic could stop colonization by an antibiotic resistant strain of bacteria given to the chicks after hatch. In Experiment 2, 120 eggs were injected with 200 µL/egg sterile saline and 120 eggs were injected with 200 µL/egg of FloraMax® into the amnion at 19 days of embryogenesis. The probiotic contained $2 \times 10^4$ CFU/200 µL consisting of a mixture of two gastrointestinal tract adapted bacteria. At hatch the chicks were randomly allocated to individual floor pens with 30 birds/pen and provided with food and water ad libitum. On days 1, 3 and 7 after hatch 12 chicks from each treatment group were selected randomly and cecal samples were obtained and used to evaluate the *Salmonella* bacterial recovery. The chicks were also weighed at days 1, 3 and 7 after hatch. As shown in FIG. 3, the chicks receiving in ovo probiotic had significantly less *Salmonella* at early time points after hatch in the cecal samples. Thus chicks receiving the probiotic may be less susceptible to early infection. In addition, as shown in FIG. 4, the chicks receiving probiotics also showed significantly increased body weights at days 3 and 7 after hatch. By day 7 after hatch weights were increased by close to 10%.

Experiment 3 was performed to evaluate if other probiotics would allow for similar effects. We chose four wild-type lactic acid bacterial probiotic candidates previously isolated from chickens and shown to grow well on MRS agar and administered each of these in ovo into the amnion at $10^4$ CFU/embryo on day 18 of embryogenesis. We saw no effect of the administration on hatchability. Samples from the gastrointestinal tract were obtained on the day of hatch and evaluated for the presence of lactic acid bacteria and the absence of gram negative bacteria. Similar results were observed. As shown in FIG. 5, all of the chicks provided lactic acid bacteria probiotic in ovo demonstrated increased lactic acid bacteria at day 1. Thus the inventors believe that gastrointestinal tract probiotics provided in ovo may increase the health of chicks at least in the first week after hatch.

Example 2—Effects of in Ovo Administration of Floramax®-B11 and Md Vaccine

This Example describes an in ovo evaluation of FloraMax®-B11 on Marek's disease HVT vaccine protective efficacy, hatchability, microbiota composition, morphometric analysis, and *Salmonella enteritidis* infection in broiler chickens Four experiments were conducted to evaluate the effect of in ovo administration of FloraMax®-B11 (FM) on Marek's disease (MD) herpesvirus of turkeys (HVT) vaccine protective efficacy, hatchability, microbiota composition, morphometric analysis and *Salmonella enteritidis* (SE) infection in chickens. In Exp. 1, day 18 White Leghorn embryos were randomly distributed in four groups: 1) HVT vaccinated in ovo and no Marek's disease virus (MDV) challenge; 2), HVT+FM vaccinated in ovo and no MDV challenge; 3) HVT vaccinated in ovo and challenge with virulent MDV (vMDV; strain 583A); 4), HVT+FM vaccinated in ovo and challenge with vMDV. Exp. 2 was designed exactly the same as Exp. 1 but chicks were challenged with very virulent MDV (vvMDV; strains Md5 and 612). In both experiments, birds were monitored until 8 wk of age, and tested for MD incidence. Exp. 3 and 4, day 18 commercial broiler embryos were injected in ovo with either saline or FM to measure hatchability and gastrointestinal composition. In addition, in Exp. 4, all chickens that hatched were then orally gavaged with SE at hatch and kept for 7 d to monitor post hatch BW. In Exp. 1 and 2, there was no significant difference (P>0.05) between MD percentage in birds vaccinated with HVT alone or HVT+FM. In Exp. 3 and 4, administration of the probiotic did not negatively affect hatchability, but did reduce lactose positive Gram negative bacteria. Further, increase in BW was associated with higher villi surface area in ileum in chickens that received the probiotic as well as a significant reduction in the SE incidence. The results of this study suggest that in ovo administration of FM does not negatively impact the ability of HVT to protect against MD or hatchability of chickens, and improves BW during the first 7 d of life and decreases SE recovery in broiler chickens.

Bacterial communities living and colonizing in the gastrointestinal tract of animals outnumber total somatic cells of metazoans by an estimated 10-fold (Neish, 2009). Today, the microbiome is recognized as the 'forgotten organ,' operating like an organ within the host and orchestrating numerous physiological and biological functions that have a profound impact on the balance between health and disease (O'Hara and Shanahan, 2006; Tellez, 2014). Early establishment of the microbiome have been reported to improve the assembly of the gut-associated lymphoid tissue (Martin et al., 2010), intervene in the development of the immune system (Mc-Fall-Ngai, 2007), maintain mucosal barrier integrity (Duerkop et al., 2009), modulate proliferation of enterocytes (Moran, 2007), adjust blood flow (Sekirov et al., 2010), regulate the enteric nervous system (Tlaskalová-Hogenová et al., 2011), and improve digestion of nutrients (Dass et al., 2007; Walter et al., 2011; Qiu et al., 2012). Essential colonization of these bacterial populations starts at birth/hatch, and is followed by progressive assembly of a complex and dynamic microbial society (Di Mauro et al., 2013).

Under commercial conditions, millions of chickens and turkeys hatch in a hostile environment, and are exposed for several hours to heat stress and potential pathogenic bacteria in the hatcheries. Increased stress along with the potential abundance of pathogens in the hatching cabinet leads to ideal conditions for pathogen colonization. It is generally accepted that the natural route of transmission of zoonotic pathogens such as *Salmonella*, is fecal-oral (White et al., 1997; Galanis et al., 2006). However, published studies have also suggested that airborne transmission of *Salmonella* in poultry is possible (Wathes et al., 1988; Baskerville et al., 1992; Leach et al., 1999; Fallschissel et al., 2009). Understanding the anatomical and immunological defenses of the avian respiratory tract helps to clarify this issue. Architecture of the avian respiratory tract is an important component to susceptibility and resistance to infectious agents. In day old chickens and turkeys, no or very few infiltrating lymphocytes are seen in the primary bronchi region (Fagerland and Arp, 1990; Smialek et al., 2011) and it is not until 3-4 weeks of age the lymphoid nodules are developed at these locations (Fagerland and Arp, 1993; Drolet et al., 2010). During the following week, the number of IgG, IgA or IgM-producing cells continues to increase, however, the bronchial-associated lymphoid tissue (BALT) is not mature until chickens are 6-8 weeks old (Bienenstock, 1980; Bienenstock and McDermott, 2005; De Geus, 2012). Hence, commercial neonate poultry are extremely susceptible to airborne pathogens, regardless of whether or not they are respiratory or enteric bacteria (Arshad et al., 1998). In support of these findings, our laboratory has recently showed that transmission by the fecal-respiratory route is a viable portal of entry for *Salmonella* (Kallapura et al., 2014a,b,c). This mode of infection could explain some clinical expression of relatively low-dose infectivity under field conditions in relation to the high oral challenge dose that is typically required for infection through the oral route in laboratory studies. This also supports previous studies demonstrating fan driven spread of *Salmonella* within the hatching cabinet and hatchery incubators (Hashemzadeh et al., 2010).

Over a century ago, Eli Metchnikoff proposed the groundbreaking idea to ingest viable bacteria to improve health (Metchnikoff, 1908). This concept is more appealing today, since antimicrobial resistant bacteria have become a problem in many countries (Kiser, 1976; Dahiya et al., 2006; Teillant and Laxminarayan, 2015). The imminent ban of antibiotics in animal feed creates a challenging scenario for expansion of alternative prophylactics (Parker, 1990; Dahiya et al., 2006; You and Silbergeld, 2014). Probiotics and direct-fed microbials are becoming accepted as one of the best tools on keeping gastrointestinal health and promoting performance in poultry raised without antibiotics (Dominguez-Bello and Blaser, 2008). In addition to improving intestinal microbial balance, metabolism, and gut integrity (Isolauri et al., 2002; Salminen and Isolauri, 2006), studies have also shown that some probiotics have anti-inflammatory (Borchers et al., 2009; Lyte, 2011), anti-oxidant (Farnell et al., 2006; Tao et al., 2006; Zareie et al., 2006; Segawa et al., 2011; Howarth and Wang, 2013), and enhanced barrier integrity properties (Yu et al., 2012). Furthermore, several researchers have confirmed benefits of probiotics on innate immunity (Alvarez-Olmos and Oberhelman, 2001; Vanderpool et al., 2008; Molinaro et al., 2012) as well as humoral immunity (Arvola et al., 1999; Haghighi et al., 2006; Howarth and Wang, 2013).

FloraMax®-B11 is a defined lactic acid bacteria (LAB) probiotic culture that has demonstrated an accelerated development of normal microflora in chickens and turkeys. It provides increased resistance to *Salmonella* spp. infections (Farnell et al., 2006; Higgins et al., 2007, 2008, 2010; Vicente et al., 2007; Menconi et al., 2011, 2013; Tellez et al., 2012; Biloni et al., 2013; Delgado et al., 2014), reduces idiopathic diarrhea in commercial turkey brooding houses (Higgins et al., 2005), as well as increased performance and reduced costs in poultry (Torres-Rodriguez et al., 2007; Vicente et al., 2008). However, no studies have been evaluated for administration of FloraMax®-B11 in ovo, and the only practical and reliable way to evaluate this route of administration, would be mixing it with the diluent of the Marek's disease (MD) vaccine. Hence, the objective of the present study was to evaluate the effect of the in ovo administration of FloraMax®-B11 on MD vaccine herpesvirus of turkeys (HVT) protective efficacy, hatchability, microbiota composition, morphometric analysis, and SE infection in chickens.

Materials and Methods

Probiotic Culture

FloraMax®-B11 (Pacific Vet Group USA Inc., Fayetteville, Ark.) is a defined probiotic culture derived from poultry gastrointestinal origin that contains proprietary strains of LAB.

The following biological materials were deposited under the terms of the Budapest Treaty at Agricultural Research Culture Collection (NRRL), International Depository Authority, 1815 N. University St., Peoria, Ill., 61604, USA, on Apr. 1, 2014 and given the following accession numbers:

| Deposit of Biological Material | | |
|---|---|---|
| Identification | Accession Number | Date of Deposit |
| *Weissella confusa* FM46 | NRRL B-50961 | Apr. 1, 2014 |
| *Pediococcus acidilactaci* FM18 | NRRL B-50964 | Apr. 1, 2014 |

The strains have been deposited under conditions that assure that access to the culture will be available during the pendency of this patent application to one determined by foreign patent laws to be entitled thereto. The deposits represent a substantially pure culture of the deposited strain. The deposits are available as required by foreign patent laws in countries wherein counterparts of the subject application or its progeny are filed. However, it should be understood that the availability of a deposit does not constitute a license to practice the subject invention in derogation of patent rights granted by governmental action.

In Ovo Evaluation of FloraMax®-B11 on Marek's Disease HVT Vaccine

Chickens and Viruses

Maternal-antibody-negative, White Leghorn $15_5 \times 7_1$ chickens were used in these experiments (Bacon et al., 2000). These MD-susceptible chickens were from an SPF breeding flock with no MD vaccinations or exposure that tested negative for MDV antibodies, exogenous avian leukosis virus, and reticuloendotheliosis virus by routine surveillance testing. All birds were housed in negative-pressure Horsfall-Bauer isolators, and experiments were conducted following approval by the USDA Avian Disease and Oncology Laboratory (ADOL) Animal Care and Use Committee. Viruses were propagated on primary duck embryo fibroblasts (DEF) maintained in Leibovitz L-15 medium plus McCoy 5A medium (1:1), supplemented with 2.5% bovine serum and antibiotics (Witter et al., 1980). In experiment 1, chickens were challenged with the MDV strain 583, a virulent (v) strain. In experiment 2, chickens were challenged with MDV strains Md5 or 612, both very virulent (vv). HVT is a commercial vaccine, and was prepared and utilized as recommended by the manufacturer (Marek's Disease Vaccine Merial Select, Serotype 3, Live Virus, HVT)

Experimental Design

Experiment 1

Chicks were randomly distributed into four groups (each with 17 birds) in two independent trials: 1) HVT vaccinated in ovo and no MDV challenge; 2) HVT+FloraMax®-B11 vaccinated in ovo and no MDV challenge; 3) HVT vaccinated in ovo and challenged with MDV; 4) HVT+FloraMax®-B11 vaccinated in ovo and challenged with MDV. MD vaccine was administered in ovo at the manufacturer recommended dosage either alone or with FloraMax®-B11 ($10^4$ cfu). Birds were monitored until 8 wk of age, then humanely euthanized and evaluated for MD incidence. Chickens were considered MD positive if peripheral nerve enlargements, tumors, or both were present at necropsy. When enlarged nerves or gross tumors were in question, tissue samples were collected and processed for microscopic evaluation. Chicks that died during the first wk of placement were considered nonspecific chick mortalities and were excluded from the experiment.

Experiment 2

The identical conditions were used as described for experiment 1 except that MDV strains Md5 and 612 were used instead of strain 583A and the experiment included only one trial.

Effect of in Ovo Application of Floramax®-B11 on Hatchability and Microbiota Composition Experiment 3 consisted of three independent trials. Eighteen-day-old embryos were obtained from Cobb-Vantress (Siloam Springs, Ark.). In each trial, eggs were candled and inoculated with either saline or $10^4$ cfu of FloraMax®-B11 via in ovo injection into the amnion. The two treatment groups were placed in separate hatchers to avoid cross contamination. On d 21, chicks were pulled from hatchers and hatchability was determined. In each trial, 12 chickens from each group were humanely euthanized to evaluate gastrointestinal composition on selective media as describe below.

Enumeration of Bacteria

For trial 1, the whole gut (ventriculus to cecum) was aseptically removed. For trials 2 and 3, the fore gut (ventriculus to Meckel's diverticulum) and hind gut (Meckel's diverticulum to cecum) were removed separately. Sections were collected into sterile bags and homogenized. Samples were weighed and 1:4 wt/vol dilutions were made with sterile 0.9% saline. Ten-fold dilutions of each sample, from each group were made in a sterile 96 well Bacti flat bottom plate and the diluted samples were plated on two different culture media; to evaluate total number of LAB in Man Rogosa Sharpe (Difco™ Lactobacilli MRS Agar VWR cat. no. 90004-084, Suwanee, Ga. 30024); total lactose positive Gram negative bacteria in MacConkey (VWR cat. no. 89429-342, Suwanee, Ga. 30024).

Evaluation of In Ovo Administration of Floramax®-B11 on Body Weight, *Salmonella enteritidis* Recovery, and Morphometric Analysis in Broiler Chickens In experiment 4, the challenge organism used in all experiments was a poultry isolate of *Salmonella enterica* (SE) serovar, *enteritidis*, bacteriophage type 13A, originally obtained from the USDA National Veterinary Services Laboratory, Ames, Iowa. This isolate was resistant to 25 µg/mL of novobiocin (NO, cat. no. N-1628, Sigma, St. Louis, Mo. 63103) and was selected for resistance to 20 µg/mL of nalidixic acid (NA, cat. no. N-4382, Sigma). For the present studies, 100 µL of SE from a frozen aliquot was added to 10 mL of tryptic soy broth (cat. no. 22092, Sigma) and incubated at 37° C. for 8 h, and passed three times every 8 h to ensure that all bacteria were in log phase growth. Post-incubation, bacterial cells were washed 3 times with sterile 0.9% saline by centrifugation at 1,800×g for 10 minutes, reconstituted in saline, quantified by densitometry with a spectrophotometer (Spectronic 20D+, Spectronic Instruments Thermo Scientific, Waltham, Mass. 02451), and diluted to an approximate concentration of $10^8$ cfu/ml. Concentrations of SE were further verified by serial dilution and plating on brilliant green agar (BGA, cat. no. 70134, Sigma) with NO and NA for enumeration of actual cfu used to challenge the chickens.

In this trial, 300 eighteen-day-old embryos were received from Cobb-Vantress. At d 18, eggs were candled and inoculated with either saline or $10^4$ cfu FloraMax®-B11 via in ovo injection into the amnion. The two treatment groups were placed in separate hatch cabinets placed in separate rooms to avoid cross contamination. On d 21, chicks were pulled from hatchers to measure hatchability. All chickens were then orally gavaged with SE on d of hatch (~$10^4$ cfu/chick). Twenty-four hours post inoculation (PI), twenty chickens were euthanized with carbon dioxide asphyxiation to determine SE intestinal colonization as described below. From these chickens, 5 samples were also taken to determine intestinal morphometric analysis as described below. BW was determined at d 1, 3, and 7. Chickens were provided ad libitum access to water and a balanced unmedicated corn-soybean diet meeting the nutrition requirements of poultry recommended by NRC (1994). All animal handling procedures were in compliance with Institutional Animal Care and Use Committee at the University of Arkansas.

Salmonella Recovery

Ceca-cecal tonsils (CCT) were homogenized and diluted with saline (1:4 by wt/vol) and tenfold dilutions were plated on BGA with NO and NA, incubated at 37° C. for 24 h to enumerate total SE colony forming units. Following plating to enumerate total SE, the CCT samples were enriched in double strength tetrathionate enrichment broth and further incubated at 37° C. for 24 h to enrich salmonellae. Following this, enrichment samples were plated on BGA with NO and NA and incubated at 37° C. for 24 h to confirm presence/absence of typical lactose-negative colonies of Salmonella.

Intestinal Morphological Analysis

For enteric morphometric analysis ileum and duodenum samples were collected (n=5). A 1-cm segment of the midpoint of the duodenum and the distal end of the lower ileum from each bird was removed and fixed in 10% buffered formaldehyde for 48 h. Each of these intestinal segments was embedded in paraffin, and a 5-µm section of each sample was placed on a glass slide and stained with hematoxylin and eosin for examination under a light microscope. All morphological parameters were measured using the ImageJ software package (http://rsb.info.nih.gov/ij/). Ten replicate measurements for each variable studied were taken from each sample, and the average values were used in statistical analysis. Villus length (VL) was measured from the top of the villus to the top of the lamina propria (Yitbarek et al., 2013). Crypt depth was measured from the base upward to the region of transition between the crypt and villus (Biloni et al., 2013). Villus width (VW) was measured at the widest area of each villus, whereas the villus:crypt ratio was determined as the ratio of villus height (VH) to crypt depth. Villus surface area (VSA) was calculated using the formula $(2\pi)(VW/2)(VL)$, (Sakamoto et al., 2000).

Statistical Analysis

All data were subjected to one-way analysis of variance as a completely randomized design using the GLM procedure of SAS (SAS Institute, 2002). Data is expressed as mean±standard error. Significant differences among the means were determined using Duncan's multiple-range test at P<0.05. MDV as well as SE incidence data were expressed as positive/total chickens (%), and the percent recovery of SE was compared using the chi-squared test of independence, testing all possible combinations to determine the significance (P≤0.001) for these studies (Zar, 1984).

Results

This study addressed three major concerns: 1) whether in ovo administration of FloraMax®-B11 mixed with MD vaccine would negatively impact vaccine efficacy, 2) the effect of in ovo administration on hatchability and microbiota composition and 3) the impact on Salmonella infections in broiler chickens. Experiment 1 consisted of two independent replicates to determine if there was any difference when birds were vaccinated in ovo with HVT only or with HVT+FloraMax®-B11 followed by challenge with vMDV. The results of the in ovo evaluation of FloraMax®-B11 on HVT vaccine efficacy in experiments 1 and 2 are summarized in Table 1. In both experiments, there was no significant difference between % MD in birds vaccinated with HVT alone or HVT+FloraMax®-B11, although numerical differences between treatment suggest that probiotics may have slightly improved protection immunity in birds challenged with MDV strain 583. This potential benefit was not apparent when we used vvMDV strains (Md5 or 612) in experiment 2 (Table 1).

TABLE 1

In ovo evaluation of FloraMax ®-B11 on HVT Marek's vaccine virus stability and incidence of disease.

|  | HVT only | HVT + FloraMax ®-B11 |
|---|---|---|
| Experiment 1 (Trial 1) | | |
| Unchallenged | 0/15 (0%) | 0/17 (0%) |
| vMDV challenge (583) | 3/17 (18%) | 0/17 (0%) |
| Experiment 1 (Trial 2) | | |
| Unchallenged | 1/16 (6%) | 0/17 (0%) |
| vMDV challenge (583) | 4/15 (27%) | 3/16 (19%) |
| Experiment 2 | | |
| Unchallenged | 0/17 (0%) | 0/17 (0%) |
| vvMDV challenge (Md5) | 10/17 (59%) | 9/17 (53%) |
| vvMDV challenge (612) | 11/17 (65%) | 13/17 (76%) |

Marek's disease HVT vaccine was administered in ovo at manufacturer labeled dosage alone or with FloraMax ®-B11 ($10^4$ cfu/g). MDV challenge was administered at 5 d of age using 500 pfu vMDV strain 583 in experiment 1, or 500 pfu vvMDV strains Md5 or 612, respectively. Birds were monitored until 8 wk of age, then euthanized and measured for MD incidence.
P > 0.05

The effect of in ovo administration of the probiotic FloraMax®-B11 on hatchability in experiment 3 is displayed in Table 2. There was no significant difference in hatchability between embryos administered probiotics or the controls. The results of the effect of in ovo application of FloraMax-B11® on microbial composition in the gastrointestinal tract of hatching broiler chickens in experiment 3 are summarized in Table 3. In trials 1 and 3, chickens treated with FloraMax®-B11 showed a significant reduction in lactose positive Gram negative bacteria recovery when compared with saline control group at d of hatch. In trial 2, the treated group had numerically lower recovery than the control group and in fact had reduced gram negatives to non-recoverable numbers. With the exception of hindgut in trial 2, a significant increase in the total number of LAB was observed in probiotic group when compared with saline treated group (Table 3).

TABLE 2

Effect of in ovo application of FloraMax ®-B11 on hatchability.

| Treatment | Trial 1 | Trial 2 | Trial 3 |
|---|---|---|---|
| Saline | 137/140 (97.8%) | 46/48 (95.8%) | 144/145 (99.3%) |
| FloraMax ®-B11 | 121/121 (100%) | 47/48 (97.9%) | 142/150 (94.6%) |

At d 18 eggs were candled and inoculated with either 0.9% saline or FloraMax ®-B11 via in ovo injection into the amnion. On d 21, chicks were pulled from hatchers and hatchability was determined, $P > 0.05$.

TABLE 3

Effect of in ovo application of FloraMax ®-B11 on microbial composition in the gastrointestinal tract of hatching broiler chickens.

| Selective media and experimental groups | Trial 1 | Trial 2 | | Trial 3 | |
|---|---|---|---|---|---|
| | Whole gut | Fore gut | Hind gut | Fore gut | Hind gut |
| Total lactose positive Gram negative bacteria/g[1] | | | | | |
| Saline | 8.24 ± 0.27 | 0.8 ± 0.5 | 1.6 ± 0.8 | 4.06 ± 0.52 | 8.54 ± 0.24 |
| FloraMax ®-B11 | 0.92 ± 0.48* | 0.0 ± 0.0 | 0.0 ± 0.0 | 0.05 ± 0.01* | 0.0 ± 0.0* |
| Total LAB/g[2] | | | | | |
| Saline | 8.70 ± 0.26 | 4.90 ± 0.5 | 7.7 ± 0.40 | 0.00 ± 0.0 | 0.84 ± 0.60 |
| FloraMax ®-B11 | 6.43 ± 0.94* | 6.20 ± 0.50* | 7.9 ± 0.40 | 4.33 ± 0.50* | 6.00 ± 0.31* |

At d 18 eggs were candled and inoculated with either saline or FloraMax ®-B11 via in ovo injection into the amnion. On d 21, chicks were pulled from the hatchers and for experiment 1, the whole gut (ventriculus to cecum) was aseptically removed. For trials 2 and 3 the fore gut (ventriculus to Meckel's diverticulum) and hind gut (Meckel's diverticulum to cecum) were removed separately.
[1]Samples were plated on MacConkey agar to evaluate total lactose positive Gram negative bacteria.
[2]Samples were plated on MRS agar to evaluate total lactic acid bacteria.
Data is expressed as mean ± standard error.
*Superscripts within columns for each plate indicate significant difference at $P < 0.05$, $n = 12$.

The results of in ovo administration of FloraMax®-B11 on hatchability, BW and SE recovery in broiler chickens of Experiment 4 are summarized in Table 4. In this experiment, no significant changes were observed in hatchability or the BW of the neonates when they were removed from the hatching cabinets; however, a significant increase in BW was observed in chickens that received the probiotic when compared with saline control groups on d 3 and 7 (Table 4). Interestingly, chickens that received the probiotic, showed a significant reduction in the incidence and total SE cfu numbers recovered from CCT when compared with saline control chickens (Table 4).

TABLE 4

Evaluation of in ovo administration of FloraMax ®-B11 on hatchability, body weight, and *Salmonella Enteritidis* recovery in broiler chickens.

| Treatment | Hatchability | Day 1 BW (g) | Day 3 BW (g) | Day 7 BW (g) | SE incidence Ceca-cecal tonsils 24 h PI | $Log_{10}$ SE/g of ceca content 24 h PI |
|---|---|---|---|---|---|---|
| Saline | 148/150 (98.6%) | 49.13 ± 0.30 [a] | 62.53 ± 0.81 [b] | 132.89 ± 3.06 [b] | 20/20 (100%) | 7.13 ± 1.01 [a] |

TABLE 4-continued

Evaluation of in ovo administration of FloraMax ®-B11 on hatchability, body weight, and *Salmonella Enteritidis* recovery in broiler chickens.

| Treatment | Hatchability | Day 1 BW (g) | Day 3 BW (g) | Day 7 BW (g) | SE incidence Ceca-cecal tonsils 24 h PI | $Log_{10}$ SE/g of ceca content 24 h PI |
|---|---|---|---|---|---|---|
| FloraMax ®-B11 | 142/150 (94.6%) | 49.72 ± 0.36 [a] | 65.42 ± 0.77 [a] | 144.98 ± 3.02 [a] | 9/20 (45%) * | 5.45 ± 1.25 [b] |

At d 18 eggs were candled and inoculated with either saline or FloraMax ®-B11via in ovo injection into the amnion. On d 21, chicks were pulled from the hatchers and were challenged with *Salmonella Enteritidis* (SE) on d of hatch ~$10^4$ cfu/chick. Incidence data is expressed as positive/total chickens (%) at 24 h post inoculation (PI), asterisk indicate significant differences P < 0.001, n = 20/group. $Log_{10}$ SE/g of ceca content is expressed as mean ± standard error.
[a,b] Superscripts within columns indicate significant differences P < 0.05, n = 12/group.

The results of the effect of in ovo application of FloraMax®-B11 on morphometric analysis of the gastrointestinal tract of hatching broiler chickens of experiment 4 are summarized in Table 5. A numerical increase in VH, VW, and VSA was observed in the treated group when compared to the controls for the duodenum. Nevertheless, embryos that received the probiotic showed a significant increase in the villus:crypt depth ratio when compared with saline control group. In the ileum, there was a significant increase in VH, VSA, and crypt depth in the probiotic treated group when compared to the control group.

TABLE 5

Evaluation of in ovo administration of FloraMax ®-B11 on morphometric analysis of the gastrointestinal tract of hatching broiler chickens

| | Villus height (μm) | Villus width (μm) | Villus surface area (mm$^2$)* | Crypt depth (μm) | VH:CD ratio** |
|---|---|---|---|---|---|
| Duodenum | | | | | |
| Control | 223.39 ± 3.55[a] | 36.01 ± 0.72[a] | 25.39 ± 0.69[a] | 49.92 ± 1.15[a] | 4.74 ± 0.14[b] |
| FloraMax ®-B11 | 234.58 ± 5.19[a] | 36.14 ± 0.60[a] | 26.87 ± 0.86[a] | 39.93 ± 0.88[b] | 6.09 ± 0.19[a] |
| Ileum | | | | | |
| Control | 148.09 ± 4.26[b] | 27.42 ± 0.86[a] | 13.10 ± 0.67[b] | 36.70 ± 1.04[b] | 4.16 ± 0.12[a] |
| FloraMax ®-B11 | 176.77 ± 5.50[a] | 29.01 ± 0.78[a] | 16.47 ± 0.80[a] | 40.55 ± 1.19[a] | 4.59 ± 0.21[a] |

[a,b]Means with different superscripts within the same column differ significantly (P < 0.05).
*Villus surface area: [2π × (villus width/2) × (villus height)]
**Villus height (VH) to crypt depth (CD) ratio.

MD is a lymphoproliferative disease of domestic chickens caused by an oncogenic α-herpesvirus (Churchill and Biggs, 1967; Calnek, 2001). The disease is associated with lymphomas, neurologic manifestations, and immune suppression (Calnek, 2001). Without a question, MD has been a major concern to the poultry industry for over half a century (Nair, 2005), and the modern poultry industry as we know it today, would not exist without the development of MD vaccines (Baigent et al., 2006; Gimeno, 2008; Parvizi et al., 2010; Silva et al., 2010; Dunn and Silva, 2012). The virus is so abundant and stable in the environment, that vaccination at the hatchery is the only effective method to control MD in commercial flocks (Witter et al., 1980, 2005; Baigent et al., 2006; Dunn et al., 2010). Due to the significant economic and immunosuppression impact, modern commercial chickens are vaccinated before they leave the hatchery.

Although, we have reported the benefits of spray application of FloraMax®-B11 in the hatcheries (Wolfenden et al., 2007), this is the first report of in ovo application of this defined probiotic, mixed with HVT vaccine simultaneously. One of the two major concerns we addressed in this study was whether in ovo administration of FloraMax®-B11 would negatively affect MD vaccine protective efficacy. The results of experiments 1 and 2, demonstrated that there was no negative impact and even possibly a small improvement of the probiotic depending on the MDV challenge strain. As far as we are aware, this is the first report showing the possibility of combining a probiotic with an in ovo MD vaccine showing no negative effect. The other major concern with in ovo application of FM was on broiler hatchability, but in every trial conducted the probiotic also showed no negative effects on hatchability.

In the present study, it was remarkable to observe that embryos, which received the probiotic before hatch, had a significant reduction in lactose positive Gram negative bacteria when compared with saline treated chickens (Table 3). Although there is extensive evidence demonstrating that this particular probiotic is able to control Salmonellae infections in poultry in both, laboratory or commercial conditions (Farnell et al., 2006; Higgins et al., 2007, 2008, 2010; Vicente et al., 2007; Menconi et al., 2011, 2013; Tellez et al., 2012; Biloni et al., 2013; Delgado et al., 2014). This current study further validated the probiotics efficacy via in ovo administration by reducing the recovery of SE when chickens were challenged at d of hatch and cultured 24 h later (Table 4). These results are in agreement with the work of De Oliveira et al. (2014) who demonstrated that in ovo colonization with probiotic could become an important method to reduce *Salmonella* and other intestinal bacterial infections in poultry.

In experiment 4, the significant increase in BW in treated chickens at d 3 and 7 (Table 4), were associated with significant morphometric changes in the duodenum and ileum observed at d 1 (Table 5). It is likely that the higher BW in the probiotic treated group was due to the increase VH, leading to more VSA leading to better nutrient absorption. These results are meaningful in context with the rapid early growth of broiler chicks. A newly hatched modern broiler chick increases its BW by 25% overnight and 5000% by 5 wk, to 2 kg (Choct, 2009). Similarly, it is also important to consider the productive life of broiler chickens. The full genetic potential of modern chickens starts at conception and the first 21 d of embryo development. During this period, variables as temperature or oxygen are important and any problem related to them could cause a big impact later in life. Hence, the 21 d of embryogenesis plus the first 7 d of life of the chicken could potentially represent between 50% to 74% of the life of a commercial broiler chicken, depending on the time they are slaughtered (56 or 77 d) (Cherian, 2011). Therefore, earlier administration of probiotics to embryos can have a profound impact on growth and overall health of the birds.

In summary, the results of the present study suggest in ovo administration of FloraMax®-B11 does not negatively affect HVT vaccine efficacy or hatchability of the chickens, and improves BW and intestinal integrity during the first 7 d of life while decreasing SE intestinal load in broiler chickens. Elucidating the role of FloraMax®-B11 on other commercial MDV vaccine strains requires further investigation; however, studies to evaluate this probiotic with HVT vaccines under commercial conditions are currently underway.

REFERENCES

Alvarez-Olmos, M. I., and R. A. Oberhelman. 2001. Probiotic agents and infectious diseases: a modern perspective on a traditional therapy. Clin. Infect. Dis. 32:1567-1576.

Arshad, M. J., M. Siddique, S. U. Rehman, and M. S. Aslam. 1998. A comparative study of respiratory phagocytic cell activities in layer chicks. Med. J. Islamic Acad. Sci. 11:107-110.

Arvola, T., K. Laiho, S. Torkkeli, H. Mykkanen, S. Salminen, L. Maunula, and E. Isolauri. 1999. Prophylactic *Lactobacillus* GG reduces antibiotic-associated diarrhea in children with respiratory infections: A randomized study. Pediatr. 104:e64-e64.

Bacon, L. D., H. D. Hunt, and H. H. Cheng. 2000. A review of the development of chicken lines to resolve genes determining resistance to diseases. Poult. Sci. 79:1082-93.

Baigent, S. J., L. P. Smith, V. K. Nair, and R. J. Currie. 2006. Vaccinal control of Marek's disease: current challenges, and future strategies to maximize protection. Vet. Immunol. Immunopathol. 112:78-86.

Baskerville, A., T. Humphrey, R. B. Fitzgeorge, R. W. Cook, H. Chart, B. Rowe, and A. Whitehead. 1992. Airborne infection of laying hens with *Salmonella enteritidis* phage type 4. Vet. Rec. 130:395.

Bienenstock, J. 1980. Bronchus-associated lymphoid tissue and the source of immunoglobulin-containing cells in the mucosa. Environ. Health Perspect. 35:39-42.

Bienenstock, J., and M. R. McDermott. 2005. Bronchus- and nasal-associated lymphoid tissues. Immunol. Rev. 206: 22-31.

Biloni, A., C. Quintana, A. Menconi, G. Kallapura, J. Latorre, C. Pixley, S. Layton, M. Dalmagro, X. Hernandez-Velasco, A. Wolfenden, B. M. Hargis, and G. Tellez. 2013. Evaluation of effects of EarlyBird associated with FloraMax-B11 on *Salmonella enteritidis*, intestinal morphology, and performance of broiler chickens. Poult. Sci. 92:2337-2346.

Borchers, A. T., C. Selmi, F. J. Meyers, C. L. Keen, and M. E. Gershwin. 2009. Probiotics and immunity. J. Gastroenterol. 44:26-46.

Calnek, B. 2001. Pathogenesis of Marek's disease virus infection. Pages 25-55 in Marek's Disease. Springer-Verlag, Berlin Heidelberg.

Cherian, G. 2011. Essential fatty acids and early life programming in meat-type birds. World Poult. Sci. J. 67:599-614.

Choct, M. 2009. Managing gut health through nutrition. Br. Poult. Sci. 50:9-15.

Churchill, A. E., and P. M. Biggs. 1967. Agent of Marek's disease in tissue culture. Nature 215:528-30.

Dahiya, J., D. Wilkie, A. Van Kessel, and M. Drew. 2006. Potential strategies for controlling necrotic enteritis in broiler chickens in post-antibiotic era. Anim. Feed Sci. Tech. 129:60-88.

Dass, N. B., A. K. John, A. K. Bassil, C. W. Crumbley, W. R. Shehee, F. P. Maurio, G. B. Moore, C. M. Taylor, and G. J. Sanger. 2007. The relationship between the effects of short-chain fatty acids on intestinal motility in vitro and GPR43 receptor activation. Neurogastroenterol. Motil. 19:66-74.

De Geus, E. D. 2012. Respiratory immune responses in the chicken; Towards development of mucosal avian influenza virus vaccines. PhD Diss. Utrecht University, the Netherlands.

Delgado, R., J. Latorre, E. Vicuña, X. Hernandez-Velasco, J. Vicente, A. Menconi, G. Kallapura, S. Layton, B. Hargis, and G. Tellez. 2014. Glycerol supplementation enhances the protective effect of dietary FloraMax-B11 against *Salmonella enteritidis* colonization in neonate broiler chickens. Poult. Sci. 93:1-7.

De Oliveira, J., E. van der Hoeven-Hangoor, I. van de Linde, R. Montijn, and J. van der Vossen. 2014. In ovo inoculation of chicken embryos with probiotic bacteria and its effect on posthatch *Salmonella* susceptibility. Poult. Sci. 93:818-829.

Di Mauro, A., J. Neu, G. Riezzo, F. Raimondi, D. Martinelli, R. Francavilla, and F. Indrio. 2013. Gastrointestinal function development and microbiota. Ital. J. Pediatr. 39:1-7.

Dominguez-Bello, M. G., and M. J. Blaser. 2008. Do you have a probiotic in your future? Microbes Infect. 10:1072-1076.

Drolet, J. P., H. Frangie, J. Guay, O. Hajoui, Q. Hamid, and B. D. Mazer. 2010. B lymphocytes in inflammatory airway diseases. Clin. Exp. Allergy 40:841-849.

Duerkop, B. A., S. Vaishnava, and L. V. Hooper. 2009. Immune responses to the microbiota at the intestinal mucosal surface. Immun. 31:368-376.

Dunn, J. R., R. L. Witter, R. F. Silva, L. F. Lee, J. Finlay, B. A. Marker, J. B. Kaneene, R. M. Fulton, and S. D. Fitzgerald. 2010. The effect of the time interval between exposures on the susceptibility of chickens to superinfection with Marek's disease virus. Avian Dis. 54:1038-1049.

Dunn, J. R., and R. F. Silva. 2012. Ability of MEQ-deleted MDV vaccine candidates to adversely affect lymphoid organs and chicken weight gain. Avian Dis. 56:494-500.

Fagerland, J. A., and L. H. Arp. 1990. A morphologic study of bronchus-associated lymphoid tissue in turkeys. Am. J. Anat. 189:24-34.

Fagerland, J. A., and L. H. Arp. 1993. Structure and development of bronchus-associated lymphoid tissue in conventionally reared broiler chickens. Avian Dis. 37:10-18.

Fallschissel, K., P. Kämpfer, and U. Jäckel. 2009. Direct detection of Salmonella cells in the air of livestock stables by real-time PCR. Ann. Occup. Hyg. 53:859-68.

Farnell, M., A. Donoghue, F. S. De Los Santos, P. Blore, B. Hargis, G. Tellez, and D. Donoghue. 2006. Upregulation of oxidative burst and degranulation in chicken heterophils stimulated with probiotic bacteria. Poult. Sci. 85:1900-1906.

Galanis, E., D. M. Lo Fo Wong, M. E. Patrick, N. Binsztein, A. Cieslik, T. Chalermchikit, A. Aidara-Kane, A. Ellis, F. J. Angulo, and H. C. Wegener. 2006. Web-based surveillance and global Salmonella distribution, 2000-2002. Emerg. Infect. Dis. 12:381-388.

Gimeno, I. M. 2008. Marek's disease vaccines: a solution for today but a worry for tomorrow? Vaccine 26:C31-C41.

Haghighi, H. R., J. Gong, C. L. Gyles, M. A. Hayes, H. Zhou, B. Sanei, J. R. Chambers, and S. Sharif. 2006. Probiotics stimulate production of natural antibodies in chickens. Clin. Vaccine Immunol. 13:975-980.

Hashemzadeh, Z., M. A. Karimi Torshizi, S. Rahimi, V. Razban, and T. Zahraei Salehi. 2010. Prevention of Salmonella colonization in neonatal broiler chicks by using different routes of probiotic administration in hatchery evaluated by culture and PCR techniques. J. Agri. Sci. Tech. 12:425-432.

Higgins, S., A. Torres-Rodriguez, J. Vicente, C. Sartor, C. Pixley, G. Nava, G. Tellez, J. Barton, and B. Hargis. 2005. Evaluation of intervention strategies for idiopathic diarrhea in commercial turkey brooding houses. J. Appl. Poult. Res. 14:345-348.

Higgins, J., S. Higgins, J. Vicente, A. Wolfenden, G. Tellez, and B. Hargis. 2007. Temporal effects of lactic acid bacteria probiotic culture on Salmonella in neonatal broilers. Poult. Sci. 86:1662-1666.

Higgins, J. P., R. L. Andreatti Filho, S. E. Higgins, A. D. Wolfenden, G. Téllez, and B. M. Hargis. 2008. Evaluation of Salmonella-lytic properties of bacteriophages isolated from commercial broiler houses. Avian Dis. 52:139-142.

Higgins, J., S. Higgins, A. Wolfenden, S. Henderson, A. Torres-Rodriguez, J. Vicente, B. Hargis, and G. Tellez. 2010. Effect of lactic acid bacteria probiotic culture treatment timing on Salmonella enteritidis in neonatal broilers. Poult. Sci. 89:243-247.

Howarth, G. S., and H. Wang. 2013. Role of endogenous microbiota, probiotics and their biological products in human health. Nutrients 5:58-81.

Isolauri, E., P. Kirjavainen, and S. Salminen. 2002. Probiotics: a role in the treatment of intestinal infection and inflammation? Gut 50:iii54-iii59.

Kallapura, G., X. Hernandez-Velasco, N. R. Pumford, L. R. Bielke, B. M. Hargis, G. Tellez. 2014a. Evaluation of respiratory route as a viable portal of entry for Salmonella in poultry. Vet. Med. Res. Rep. 5; 59-73.

Kallapura G., M. H. Kogut, M. J. Morgan, N. R. Pumford, L. R. Bielke, A. D. Wolfenden, O B. Faulkner, Latorre J. D., Menconi A., Hernandez-Velasco X., V. A. Kuttappan, B. M. Hargis and G. Tellez. 2014b. Fate and dissemination of Salmonella Senftenberg post oral, intratracheal or intravenous challenge in broiler chickens. Avian Pathol. 43:305-309. doi: 10.1080/03079457.2014.923554.

Kallapura, G., R. N. Pumford, X. Hernandez-Velasco, B. M. Hargis, G. Tellez. 2014c. Mechanisms Involved in lipopolysaccharide derived ROS and RNS oxidative stress and septic shock. J. Microbiol. Res. Rev. 2:6-11.

Kiser, J. 1976. A perspective on the use of antibiotics in animal feeds. J. Anim. Sci. 42:1058-1072.

Leach, S. A., A. Williams, A. C. Davies, J. Wilson, P. D. Marsh, and T. J. Humphrey. 1999. Aerosol route enhances the contamination of intact eggs and muscle of experimentally infected laying hens by Salmonella typhimurium DT104. FEMS Microbiol. Lett. 171:203-207.

Lyte, M. 2011. Probiotics function mechanistically as delivery vehicles for neuroactive compounds: microbial endocrinology in the design and use of probiotics. Bioessays. 33:574-581.

Martin, R., A. J. Nauta, K. Ben Amor, L. M. Knippels, J. Knol, and J. Garssen. 2010. Early life: gut microbiota and immune development in infancy. Benef. Microbes 1:367-382.

McFall-Ngai, M. 2007. Adaptive immunity: care for the community. Nature 445:153-153.

Menconi, A., A. Wolfenden, S. Shivaramaiah, J. Terraes, T. Urbano, J. Kuttel, C. Kremer, B. Hargis, and G. Tellez. 2011. Effect of lactic acid bacteria probiotic culture for the treatment of Salmonella enterica serovar Heidelberg in neonatal broiler chickens and turkey poults. Poult. Sci. 90:561-565.

Menconi, A., A. Reginatto, A. Londero, N. Pumford, M. Morgan, B. Hargis, and G. Tellez. 2013. Effect of organic acids on Salmonella Typhimurium infection in broiler chickens. Int. J. Poult. Sci. 12.

Metchnikoff E. 1908. The prolongation of life: optimistic studies. Putnam, New York.

Molinaro, F., E. Paschetta, M. Cassader, R. Gambino, and G. Musso. 2012. Probiotics, prebiotics, energy balance, and obesity: mechanistic insights and therapeutic implications. Gastroenterol. Clin. North Am. 41:843-854. doi: 10.1016/j.gtc.2012.08.009.

Moran, N. A. 2007. Symbiosis as an adaptive process and source of phenotypic complexity. Proc. Natl. Acad. Sci. USA. 104:8627-8633.

Nair, V. 2005. Evolution of Marek's disease—a paradigm for incessant race between the pathogen and the host. Vet. J. 170:175-83.

NRC. 1994. Nutrient Requirements of Poultry. 9th rev. ed. Natl. Acad. Press, Washington, D.C.

Neish, A. S. 2009. Microbes in gastrointestinal health and disease. Gastroenterol. 136:65-80.

O'Hara, A. M., and F. Shanahan. 2006. The gut flora as a forgotten organ. EMBO Rep. 7:688-693.

Parker, D. S. 1990. Manipulation of the functional activity of the gut by dietary and other means (antibiotics/probiotics) in ruminants. J. Nutr. 120:639-648.

Parvizi, P., M. F. Abdul-Careem, K. Haq, N. Thanthrige-Don, K. A. Schat, and S. Sharif. 2010. Immune responses against Marek's disease virus. Anim. Health Res. Rev. 11:123-134. doi: 10.1017/S1466252310000022.

Qiu, R., J. Croom, R. A. Ali, A. L. Ballou, C. D. Smith, C. M. Ashwell, H. M. Hassan, C. C. Chiang, and M. Koci. 2012. Direct fed microbial supplementation repartitions host energy to the immune system. J. Anim. Sci. 90:2639-2651.

SAS Institute. 2002. SAS User Guide. Version 9.1. SAS Institute Inc., Cary, N.C.

Sakamoto, K., H. Hirose, A. Onizuka, M. Hayashi, N. Futamura, Y. Kawamura, and T. Ezaki. 2000. Quantitative study of changes in intestinal morphology and mucus gel on total parenteral nutrition in rats. J. Surg. Res. 94:99-106.

Salminen, S., and E. Isolauri. 2006. Intestinal colonization, microbiota, and probiotics. J. Pediatr. 149:S115-S120.

Segawa, S., M. Fujiya, H. Konishi, N. Ueno, N. Kobayashi, T. Shigyo, and Y. Kohgo. (2011). Probiotic-derived polyphosphate enhances the epithelial barrier function and maintains intestinal homeostasis through integrin-p38 MAPK pathway. PLoS ONE 6: e23278.

Sekirov, I., S. L. Russell, L. C. Antunes, and B. B. Finlay. 2010. Gut microbiota in health and disease. Physiol. Rev. 90:859-904.

Silva, R. F., J. R. Dunn, H. H. Cheng, and M. Niikura. 2010. A MEQ-deleted Marek's disease virus cloned as a bacterial artificial chromosome is a highly efficacious vaccine. Avian Dis. 54:862-869.

Smialek, M., B. Tykalowski, T. Stenzel, and A. Koncicki. 2011. Local immunity of the respiratory mucosal system in chickens and turkeys. Pol. J. Vet. Sci. 14:291-297.

Tao, Y., K. A. Drabik, T. S. Waypa, M. W. Musch, J. C. Alverdy, O. Schneewind, E. B. Chang, and E. O. Petrof. 2006. Soluble factors from *Lactobacillus* GG activate MAPKs and induce cytoprotective heat shock proteins in intestinal epithelial cells. Am. J. Physiol. Physiol. 290: C1018-C1030.

Teillant, A., and R. Laxminarayan. 2015. Economics of antibiotic use in U.S. swine and poultry production. Choices 30:1.

Tellez, G., C. Pixley, R. E. Wolfenden, S. L. Layton, and B. M. Hargis. 2012. Probiotics/direct fed microbials for *Salmonella* control in poultry. Food Res. Int. 45:628-633.

Tellez, G. 2014. Prokaryotes versus Eukaryotes: Who is hosting whom? Front. Vet. Sci. 1:1-6.

Tlaskalová-Hogenová, H., R. Štěpánková, H. Kozáková, T. Hudcovic, L. Vannucci, L. Tučková, P. Rossmann, T. Hrnčíř, M. Kverka, Z. Zákostelská, K. Klimešová, J. Přibylová, J. Bártová, D. Sanchez, P. Fundová, D. Borovská, D. Srůtková, Z. Zídek, M. Schwarzer, P. Drastich, and D. P. Funda. 2011. The role of gut microbiota (commensal bacteria) and the mucosal barrier in the pathogenesis of inflammatory and autoimmune diseases and cancer: contribution of germ-free and gnotobiotic animal models of human diseases. Cell. Mol. Immunol. 8:110-120.

Torres-Rodriguez, A., S. Higgins, J. Vicente, A. Wolfenden, G. Gaona-Ramirez, J. Barton, G. Tellez, A. Donoghue, and B. Hargis. 2007. Effect of lactose as a prebiotic on turkey body weight under commercial conditions. J. Appl. Poult. Res. 16:635-641.

Vanderpool, C., F. Yan, and D. B. Polk. 2008. Mechanisms of probiotic action: implications for therapeutic applications in inflammatory bowel diseases. Inflamm. Bowel Dis. 14:1585-1596.

Vicente, J., A. Wolfenden, A. Torres-Rodriguez, S. Higgins, G. Tellez, and B. Hargis. 2007. Effect of a *Lactobacillus* species-based probiotic and dietary lactose prebiotic on turkey poult performance with or without *Salmonella enteritidis* challenge. J. Appl. Poult. Res. 16:361-364.

Vicente, J. L., A. Torres-Rodriguez, S. E. Higgins, C. Pixley, G. Tellez, A. M. Donoghue, and B. M. Hargis. 2008. Effect of a selected *Lactobacillus* spp. based probiotic on *Salmonella enterica* serovar *enteritidis*-infected broiler chicks. Avian Dis. 52:143-146.

Walter, J., R. A. Britton, and S. Roos. 2011. Host-microbial symbiosis in the vertebrate gastrointestinal tract and the *Lactobacillus reuteri* paradigm. Proc. Natl. Acad. Sci. 108:4645-4652.

Wathes, C., W. A. Zaidan, G. R. Pearson, M. Hinton, and N. Todd. 1988. Aerosol infection of calves and mice with *Salmonella* Typhimurium. Vet. Rec. 123:590-594.

White, P. L., A. R. Baker, and W. O. James. 1997. Strategies to control *Salmonella* and *Campylobacter* in raw poultry products. Rev. Sci. Tech. 16:525-41.

Witter, R. L., J. M. Sharma, and A. M. Fadly. 1980. Pathogenicity of variant Marek's disease virus isolants in vaccinated and unvaccinated chickens. Avian Dis. 24:210-232.

Wolfenden, A., C. Pixley, J. Higgins, S. Higgins, J. Vicente, A. Torres-Rodriguez, B. Hargis, and G. Tellez. 2007. Evaluation of spray application of a *Lactobacillus*-based probiotic on *Salmonella enteritidis* colonization in broiler chickens. Int. J. Poult. Sci. 6:493-496.

Yitbarek, A., J. C. Rodriguez-Lecompte, H. M. Echeverry, P. Munyaka, N. Barjesteh, S. Sharif, G. Camelo-Jaimes. 2013. Performance, histomorphology, and toll-like receptor, chemokine, and cytokine profile locally and systemically in broiler chickens fed diets supplemented with yeast-derived macromolecules. Poult. Sci. 92:2299-2310. doi: 10.3382/ps.2013-03141.

You, Y., and E. K. Silbergeld. 2014. Learning from agriculture: understanding low-dose antimicrobials as drivers of resistome expansion. Front. Microbiol. 5:284.

Yu, Q., L. Zhu, Z. Wang, P. Li, and Q. Yang. 2012. *Lactobacillus delbrueckii* ssp. *lactis* R4 prevents *Salmonella* Typhimurium SL1344-induced damage to tight junctions and adherens junctions. J. Microbiol. 50:613-617.

Zar, J. 1984. Biostatistical Analysis. 2nd ed. Prentice Hall, Upper Saddle River, N.J.

Zareie, M., K. Johnson-Henry, J. Jury, P. C. Yang, B. Y. Ngan, D. M. McKay, J. D. Soderholm, M. H. Perdue, and P. M. Sherman. 2006. Probiotics prevent bacterial translocation and improve intestinal barrier function in rats following chronic psychological stress. Gut 55:1553-1560.

We claim:

1. A composition comprising a probiotic and a Marek's Disease vaccine, wherein the probiotic comprises a lactic acid bacteria genus selected from the group consisting of *Lueconostoc, Staphylococcus, Weissella, Pediococcus* and combinations thereof.

2. The composition of claim 1, further comprising a diluent.

3. The composition of claim 2, wherein the diluent comprises dimethyl sulfoxide.

4. The composition of claim 2, wherein the diluent comprises the diluent supplied with the Marek's Disease Vaccine.

5. The composition of claim 2, wherein the diluent comprises a carbohydrate, a phosphate buffer and NZ amine.

6. The composition of claim 5, wherein the carbohydrate is sucrose.

7. The composition of claim 1, wherein the lactic acid bacteria had been selected for gut adaptation in poultry.

8. The composition of claim 1, wherein the probiotic comprises a lactic acid bacteria from the genus *Weissella* and a lactic acid bacteria from the genus *Pediococcus*.

9. The composition of claim 8, wherein the probiotic comprises a lactic acid bacteria from the species *Weissella cibaria*, a lactic acid bacteria from the species *Pediococcus acidilactici*, or both species.

10. The composition of claim 1, wherein the probiotic comprises one or both of NRRL B-50961 and NRRL B-50964.

11. The composition of claim 1, wherein the Marek's Disease vaccine comprises a HVT vaccine.

12. The composition of claim 11, wherein the HVT vaccine comprises the FC-126 strain of turkey herpesvirus.

13. The composition of claim 1, wherein the Marek's Disease vaccine comprises an attenuated MDV.

14. The composition of claim 13, wherein the attenuated MDV is selected from the group consisting of SB-1, 301B/1, R2/23 and CVI988.

15. A method of treating a subject comprising administering to the subject any one of the compositions of claim 1.

16. A kit comprising a probiotic and a Marek's Disease vaccine, wherein the probiotic comprises a lactic acid bacteria genus selected from the group consisting of *Lueconostoc, Staphylococcus, Weissella, Pediococcus* and combinations thereof.

* * * * *